United States Patent
Yamada et al.

(10) Patent No.: US 10,639,823 B2
(45) Date of Patent: May 5, 2020

(54) MICRONEEDLE-ARRAY MANUFACTURING APPARATUS, MICRONEEDLE-ARRAY MANUFACTURING METHOD, AND PRODUCT HAVING THE MICRONEEDLE ARRAY

(71) Applicants: NISSHA PRINTING CO., LTD., Kyoto-shi, Kyoto (JP); BIOSERENTACH CO., LTD., Kyoto-shi, Kyoto (JP)

(72) Inventors: Shinya Yamada, Kyoto (JP); Masateru Chiyama, Kyoto (JP); Kensaku Akita, Kyoto (JP); Takako Ueno, Kyoto (JP); Yuko Ide, Kyoto (JP); Sachi Nagai, Kyoto (JP); Osanobu Akao, Kyoto (JP); Ichiro Ono, Sapporo (JP); Kanji Takada, Kyoto (JP)

(73) Assignees: NISSHA PRINTING CO., LTD., Kyoto (JP); BIOSERENTACH CO., LTD., Kyoto (JP)

( * ) Notice: Subject to any disclaimer, the term of this patent is extended or adjusted under 35 U.S.C. 154(b) by 0 days.

(21) Appl. No.: 15/535,663

(22) PCT Filed: Dec. 14, 2015

(86) PCT No.: PCT/JP2015/084943
§ 371 (c)(1),
(2) Date: Jun. 13, 2017

(87) PCT Pub. No.: WO2016/098730
PCT Pub. Date: Jun. 23, 2016

(65) Prior Publication Data
US 2017/0348880 A1 Dec. 7, 2017

(30) Foreign Application Priority Data
Dec. 15, 2014 (JP) .................................. 2014-252907

(51) Int. Cl.
*A61M 37/00* (2006.01)
*B29C 39/24* (2006.01)
(Continued)

(52) U.S. Cl.
CPC ............. *B29C 39/24* (2013.01); *A61M 37/00* (2013.01); *A61M 37/0015* (2013.01);
(Continued)

(58) Field of Classification Search
CPC ....................... B29C 39/24; A61M 2037/0053
See application file for complete search history.

(56) References Cited

U.S. PATENT DOCUMENTS 6,395,326 B1   5/2002 Castro et al.
2008/0269685 A1  10/2008 Singh et al.
(Continued)

FOREIGN PATENT DOCUMENTS

JP   2010-184102 A   8/2010
JP   2012-196426 A   10/2012
(Continued)

OTHER PUBLICATIONS

McGrath, Production of Dissolvable Microneedles Using an Atomised Spraty Process: Effect of Microneedle Composition on Skin Penetration, May 29, 2013, Elsevier, European Journal of Pharmaceutics and Biopharmaceutics 86, 201-202 (Year: 2013).*
(Continued)

*Primary Examiner* — Matthew J Daniels
*Assistant Examiner* — Andrew L Swanson
(74) *Attorney, Agent, or Firm* — Global IP Counselors, LLP

(57) ABSTRACT

A product having a microneedle array is provided wherein the composition distribution has been adjusted with good accuracy. A droplet-delivery apparatus of a microneedle-array manufacturing apparatus is configured capable of
(Continued)

delivering, to each recessed part, droplets of a raw-material liquid in a prescribed amount that is less than the capacity of the recessed part. An aligning apparatus can align the relative position of the droplet-delivery apparatus and a mold such that the droplets from the droplet-delivery apparatus are caused to land in each of the recessed parts. The droplet-delivery apparatus delivers a plurality of the droplets to each of the recessed parts; and the aligning apparatus aligns the relative position of the droplet-delivery apparatus and the mold such that a second droplet lands in each of the recessed parts on the center part side of a first droplet.

9 Claims, 17 Drawing Sheets

(51) Int. Cl.
*B81B 1/00* (2006.01)
*B05B 12/12* (2006.01)
*B29C 65/00* (2006.01)
*B29L 31/00* (2006.01)

(52) U.S. Cl.
CPC .......... *B05B 12/122* (2013.01); *B29C 65/004* (2013.01); *B81B 1/00* (2013.01); *A61M 2037/0053* (2013.01); *B29L 2031/7544* (2013.01)

(56) References Cited

U.S. PATENT DOCUMENTS

| | | | |
|---|---|---|---|
| 2011/0276003 A1* | 11/2011 | Luttge | A61M 37/0015 604/173 |
| 2011/0316919 A1 | 12/2011 | Baldy, Jr. et al. | |
| 2012/0027810 A1* | 2/2012 | Chen | A61M 37/0015 424/400 |
| 2012/0078189 A1 | 3/2012 | Ogawa et al. | |
| 2013/0292868 A1* | 11/2013 | Singh | A61K 9/0021 264/102 |
| 2014/0052067 A1 | 2/2014 | Sausse et al. | |
| 2014/0168293 A1* | 6/2014 | Moreau | B41J 2/15 347/2 |
| 2017/0050010 A1* | 2/2017 | McAllister | A61M 37/0015 |
| 2017/0057124 A1* | 3/2017 | Wakamatsu | A61M 37/00 |

FOREIGN PATENT DOCUMENTS

| | | |
|---|---|---|
| JP | 2012-200572 A | 10/2012 |
| JP | 2014-082975 A | 5/2014 |
| JP | 2014-519344 A | 8/2014 |
| JP | 2014-199881 A | 10/2014 |
| WO | 2009/065087 A1 | 5/2009 |

OTHER PUBLICATIONS

Partial Supplementary Search Report in the corresponding European Patent Application No. 15869935.5 dated Nov. 24, 2017.
International Search Report in PCT/JP2015/084943 dated Feb. 9, 2016.

* cited by examiner

MICRONEEDLE-ARRAY MANUFACTURING APPARATUS, MICRONEEDLE-ARRAY MANUFACTURING METHOD, AND PRODUCT HAVING THE MICRONEEDLE ARRAY

CROSS-REFERENCE TO RELATED APPLICATION

This U.S. National stage application claims priority under 35 U.S.C. § 119(a) to Japanese Patent Application No. 2014-252907, filed in Japan on Dec. 15, 2014, the entire contents of Japanese Patent Application No. 2014-252907 are hereby incorporated herein by reference.

BACKGROUND

Field of the Invention

The present invention relates to: a microneedle-array manufacturing apparatus for manufacturing a microneedle array comprising a plurality of microneedles; a microneedle-array manufacturing method; and a product having the microneedle array.

BACKGROUND ART

In recent years, there has been an increasing number of situations in which microneedles are used in, for example, fields related to medical care and fields related to beauty and health. For example, microneedle arrays comprising a plurality of microneedles are being used to administer drugs via the surface of the human body, such as, for example, via the skin or a mucous membrane. As an example of such a microneedle-array manufacturing method, a method is known in which a mold having a plurality of recessed parts is filled with a needle raw material using a squeegee and then dried to harden it, as described in, for example, Patent Citation 1 (Japanese Unexamined Patent Application Publication No. 2012-200572). In particular, if each microneedle is formed of a plurality of layers and the composition of each layer differs, then the microneedle-array manufacturing method as described above is convenient.

In a method in which a stamper 200, which is one type of the mold described in Patent Citation 1, and a squeegee 210 are used to alternately and repetitively fill and dry a needle raw material in the order of FIG. 18A, FIG. 18B, FIG. 18C, FIG. 18D, and FIG. 18E, there is a tendency for errors in the fill amounts of microneedle raw materials 291, 292, 293, with which recessed parts 201, 202, 203, 204 are filled, to become large. For example, differences in layer thicknesses Lh1, Lh2, Lh3, Lh4 of upper layers 231, 232, 233, 234 of microneedles 221, 222, 223, 224 adversely occur. The differences in these layer thicknesses degrade the accuracy of the composition distribution, and thereby problems occur in which the amounts of the pharmaceutical agent varies among the four microneedles 221, 222, 223, 224, large errors occur in the amount of the pharmaceutical agent as a whole, and the like.

An object of the present invention is to provide a microneedle-array manufacturing apparatus and a microneedle-array manufacturing method in which the composition distribution of a microneedle array can be adjusted with good accuracy, and to provide a product having the microneedle array wherein the composition distribution has been adjusted with good accuracy.

A plurality of aspects is explained below as the technical solution. These aspects can be arbitrarily combined as needed.

A microneedle-array manufacturing apparatus according to one aspect of the invention is a microneedle-array manufacturing apparatus for forming a microneedle array comprising a plurality of microneedles by filling a plurality of recessed parts formed in a mold with a raw-material liquid for forming the microneedles, comprising: a droplet-delivery apparatus capable of delivering, to each of the recessed parts, droplets of the raw-material liquid in a prescribed amount that is less than the capacity of the recessed part; and an aligning apparatus capable of aligning the relative position of the droplet-delivery apparatus and the mold such that the droplets from the droplet-delivery apparatus land in each of the recessed parts.

In addition, it may be configured such that: the droplet-delivery apparatus delivers a plurality of the droplets to each of the recessed parts, and the aligning apparatus aligns the relative position of the droplet-delivery apparatus and the mold such that a second droplet lands in each of the recessed parts on the center part side of a first droplet.

In addition, it may be configured such that: the aligning apparatus aligns the relative position of the droplet-delivery apparatus and the mold such that the plurality of the droplets lands, in each of the recessed parts, at sequentially differing positions from one end side to another end side, passing through the center part.

In addition, the droplet-delivery apparatus may be configured capable of delivery such that the plurality of droplets is less than the capacity of each recessed part.

In addition, it may be configured such that, in the droplet-delivery apparatus, the liquid amount of one droplet delivered at one time is less than one third of the capacity of each recessed part; and it may be configured such that the droplet-delivery apparatus and the aligning apparatus perform alignment such that three or more droplets land at differing positions inside each recessed part.

In addition, the droplet-delivery apparatus may be configured capable of separately delivering a first liquid and a second liquid, wherein components differ from one another, as the raw-material liquid; and the droplet-delivery apparatus and the aligning apparatus may be configured capable of selectively delivering—for each recessed part—the first liquid and the second liquid.

In addition, the droplet-delivery apparatus and the aligning apparatus may be configured such that the recessed parts located in a first area of the mold can be filled with a first amount of the raw-material liquid, and the recessed parts located in a second area of the mold can be filled with a second amount of the raw-material liquid.

A microneedle-array manufacturing method according to one aspect of the present invention comprises: a first filling step in which a plurality of first recessed parts of a mold is filled with a first raw-material liquid by causing a plurality of droplets of the first raw-material liquid in an amount that is less than the capacity of the first recessed part to land in the plurality of first recessed parts; and a drying step in which the first raw-material liquid of a plurality of the first recessed parts is dried, thereby forming a microneedle array comprising a plurality of microneedles.

A microneedle-array manufacturing method according to another aspect of the present invention comprises: a first filling step in which a plurality of first recessed parts of a mold is filled with a first raw-material liquid by causing a plurality of droplets of the first raw-material liquid in an amount that is less than the capacity of the first recessed part to land in the plurality of first recessed parts such that a second droplet lands in each of the first recessed parts on a center part side of a first droplet; and a drying step in which the first raw-material liquid of a plurality of the first recessed parts is dried, thereby forming a microneedle array comprising a plurality of microneedles.

A microneedle-array manufacturing method according to yet another aspect of the present invention comprises: a first filling step in which a plurality of first recessed parts of a mold is filled with a first raw-material liquid by causing a plurality of droplets of the first raw-material liquid in amounts less than the capacity of each first recessed part to land in the plurality of first recessed parts such that a second droplet lands in each first recessed part on a center part side of a first droplet; a drying step in which a microneedle array comprising a plurality of microneedles is formed by drying the first raw-material liquid in the plurality of first recessed parts; and a fastening step in which a third raw-material liquid is disposed on a surface of a porous-base member such that the third raw-material liquid covers at least part thereof, the mold is reversed, a surface on which the first recessed parts of the mold are formed is overlaid on the surface of the porous-base member with a prescribed pressure, and the third raw-material liquid is dried, and thereby microneedles, which include portions formed by the drying of the first raw-material liquid, are fastened onto the porous-base member.

In addition, the microneedle-array manufacturing method may further comprise: a second filling step in which second recessed parts of the mold are filled with a second raw-material liquid by causing droplets of the second raw-material liquid in amounts less than the capacity of each second recessed part to land in the second recessed parts; wherein, the drying step includes a step of forming the microneedles by drying the second raw-material liquid in the second recessed parts.

A product having a microneedle array according to one aspect of the present invention comprises: a first microneedle that is formed in at least one first area, includes a first composition in a peak-part layer at a tip, and includes a third composition at a next second layer; and a second microneedle that is formed in at least one second area adjacent to the at least one first area, includes a second composition in a peak-part layer at the tip, and includes a fourth composition at the next second layer; wherein, it is configured such that the type of the third composition differs from that of the first composition and the type of the fourth composition differs from that of the second composition, at least one of the type and the amount of the second composition differs from that of the first composition, and at least one of the types and the amounts of the third composition and the fourth composition differs.

A product having a microneedle array according to another aspect of the present invention comprises: a plurality of first microneedles that is formed in at least one first area and includes a first composition in peak-part layers at tips; and a plurality of second microneedles that is formed in at least one second area adjacent to the at least one first area and includes a second composition in the peak-part layers at the tips; wherein, the at least one second area is disposed such that it surrounds the at least one first area.

A product having a microneedle array according to yet another aspect of the present invention comprises: a fixed part having a curved surface; and a plurality of water-soluble microneedles that contains preset amounts of prescribed compositions and is disposed on the curved surface such that the microneedles are parallel to one another.

According to a microneedle-array manufacturing apparatus and a microneedle-array manufacturing method of the present invention, the composition distribution of a microneedle array can be adjusted with good accuracy. In addition, in a product having the microneedle array of the present invention, the composition distribution is adjusted with good accuracy.

DESCRIPTION OF EMBODIMENTS

First Embodiment

A microneedle-array manufacturing apparatus according to a first embodiment of the present invention, a microneedle-array manufacturing method, and a product having the manufactured microneedle array are explained below, with reference to the drawings.

(1) Overview of Microneedle-Array Manufacturing Apparatus

Figure 1:
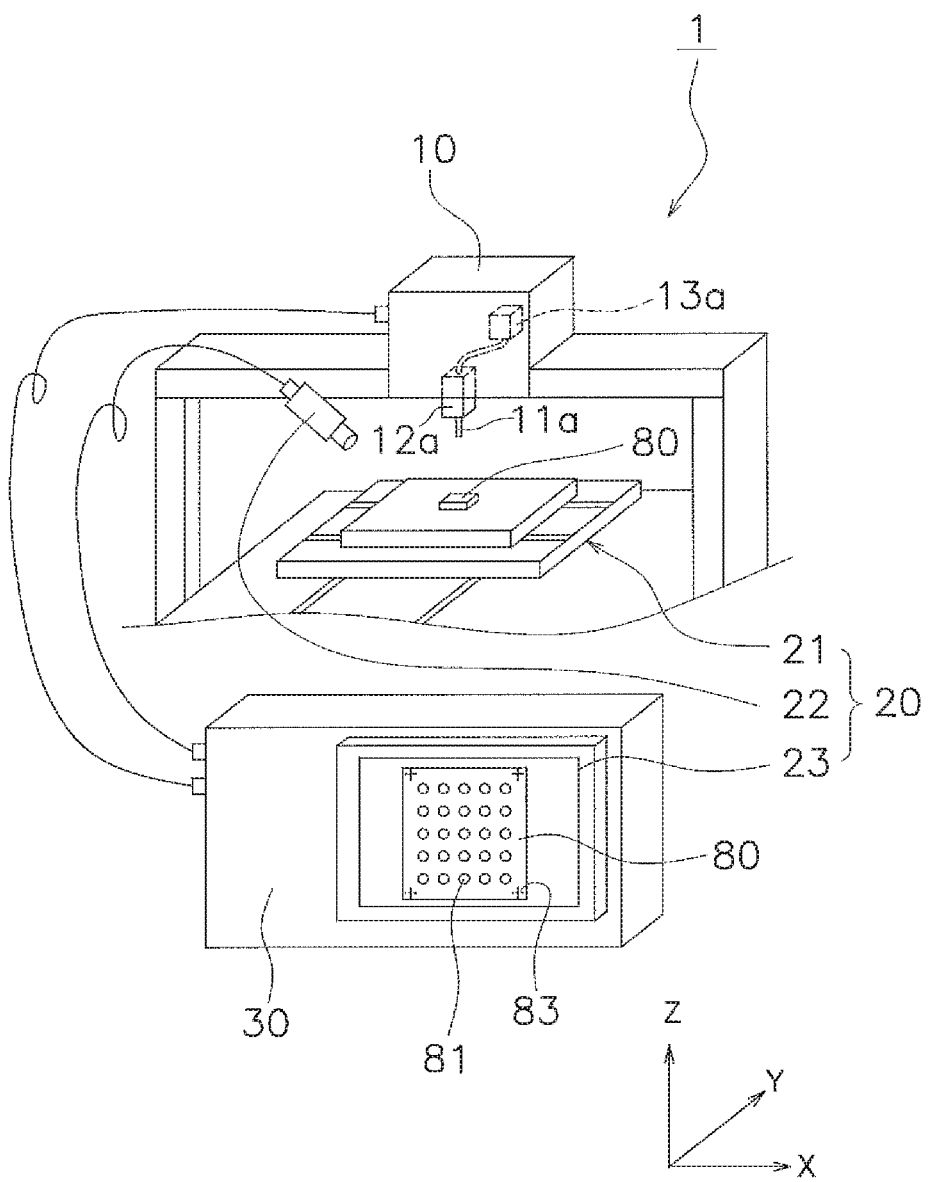
FIG. 1 is a schematic oblique view that shows an overview of a microneedle-array manufacturing apparatus according to a first embodiment.
Figure 10:
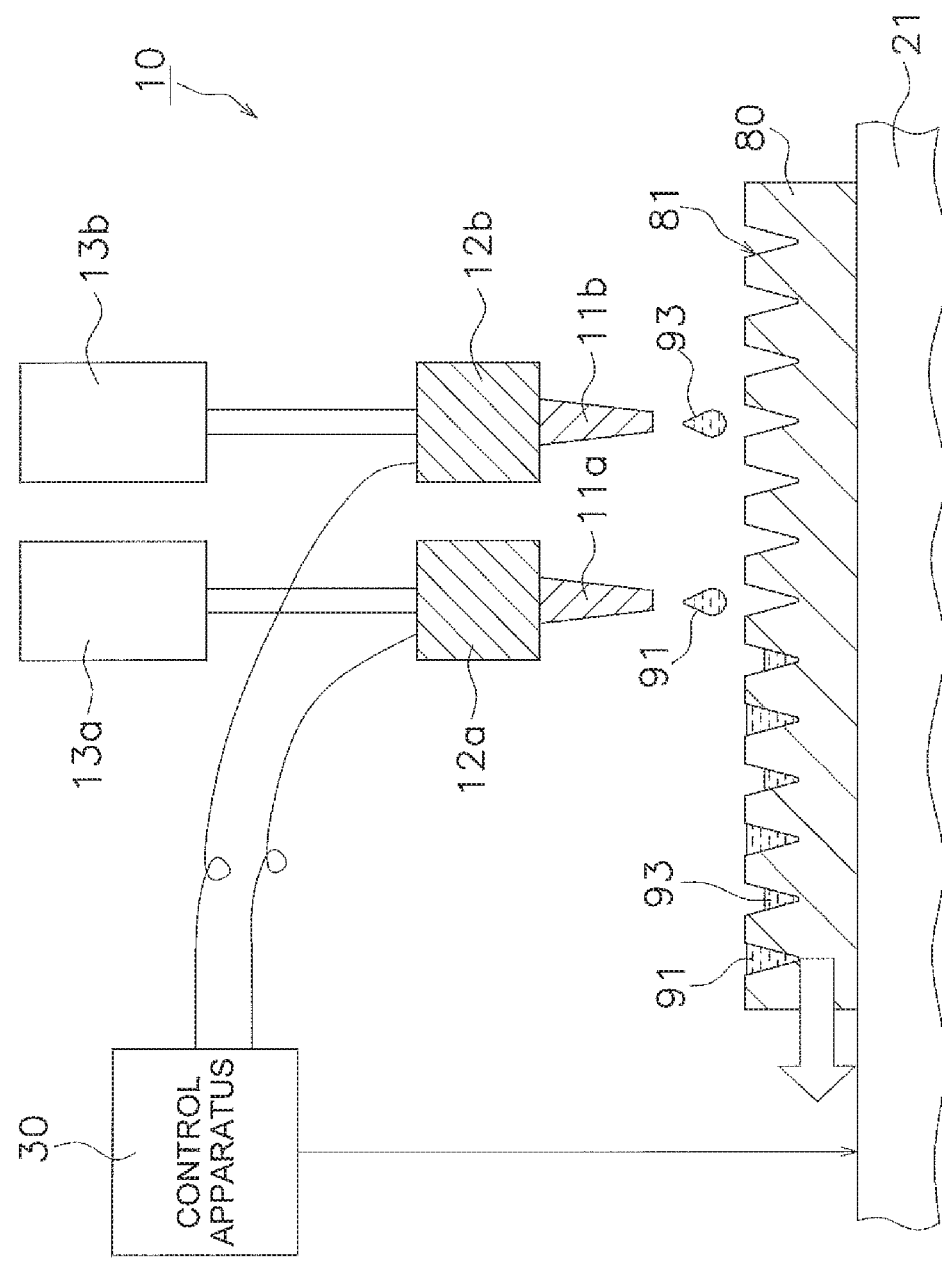
FIG. 10 is a schematic cross-sectional view for explaining the delivery of droplets to recessed parts according to a second embodiment.

FIG. 1 is a schematic oblique view that shows an overview of the microneedle-array manufacturing apparatus. As shown in FIG. 1, a microneedle-array manufacturing apparatus 1 comprises a droplet-delivery apparatus 10 and an aligning apparatus 20. The aligning apparatus 20 comprises an XYZ stage 21, a CCD camera 22, and an alignment monitor 23. The droplet-delivery apparatus 10 is provided with a nozzle 11a, which is for delivering droplets, and a cartridge 13a, which contains a raw-material liquid that is supplied to the nozzle 11a, as shown in FIG. 1. Furthermore, although not shown in FIG. 1, the droplet-delivery apparatus 10 also has another nozzle lib and another cartridge 13b, which are shown in FIG. 10.

Figure 2:
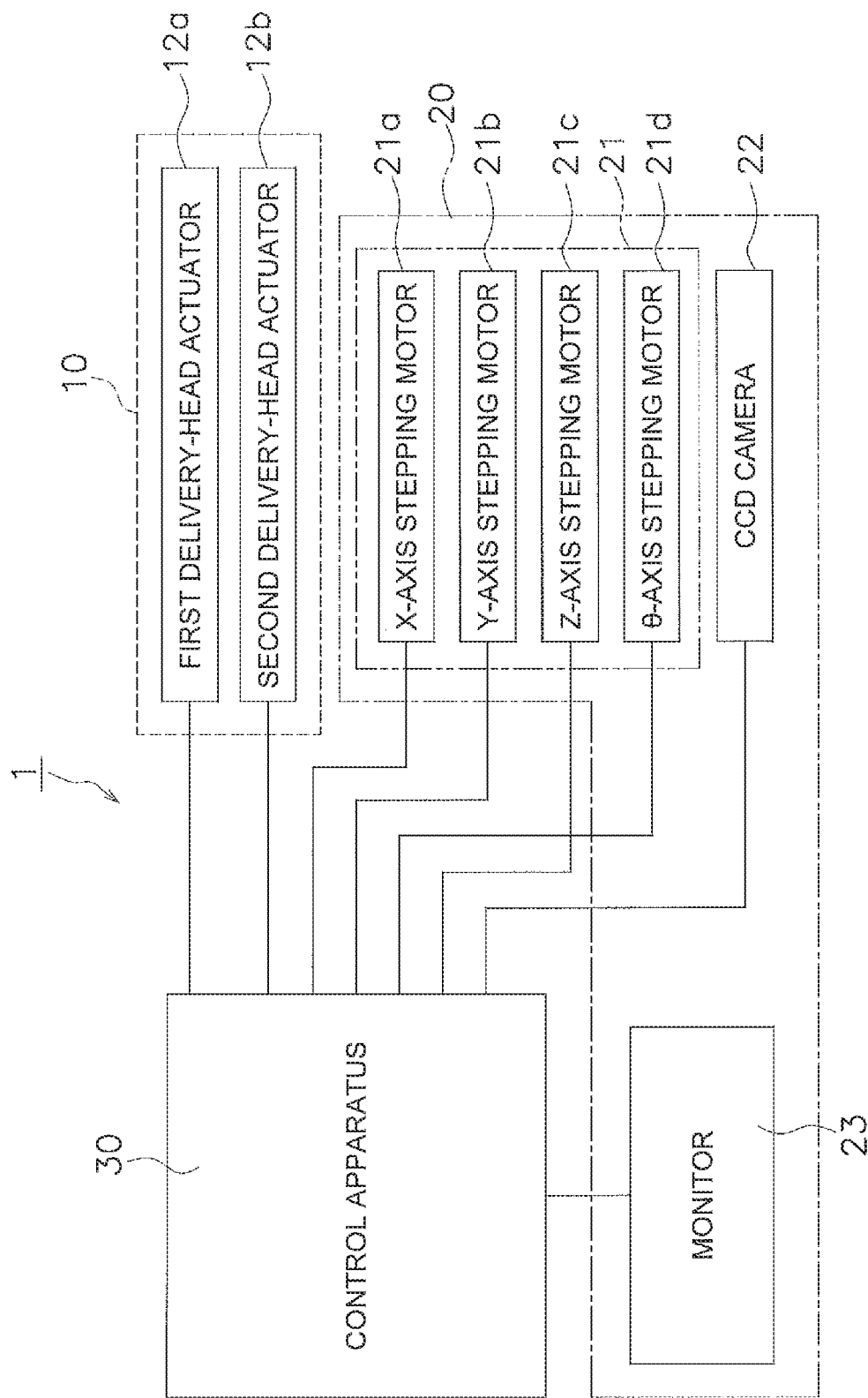
FIG. 2 is a block diagram for explaining a control system of the microneedle-array manufacturing apparatus shown in FIG. 1.

In addition, as shown in FIG. 2, from the viewpoint of the system that controls the microneedle-array manufacturing apparatus 1, the microneedle-array manufacturing apparatus 1 comprises a control apparatus 30, which controls the droplet-delivery apparatus 10 and the aligning apparatus 20. In the droplet-delivery apparatus 10, a first delivery-head actuator 12a and a second delivery-head actuator 12b are controlled by the control apparatus 30. The microneedle-array manufacturing apparatus 1 is configured such that the control apparatus 30 controls the first delivery-head actuator 12a and the second delivery-head actuator 12b, and thereby the liquid-droplet amounts delivered from the nozzles 11a, 11b can be finely adjusted. In the aligning apparatus 20, an X-axis stepping motor 21a, a Y-axis stepping motor 21b, a Z-axis stepping motor 21c, and a θ-axis stepping motor 21d of the XYZ stage 21, as well as the CCD camera 22 and the alignment monitor 23, are controlled by the control apparatus 30. A mold 80 mounted on the XYZ stage 21 is moved in an X axial direction by the X-axis stepping motor 21a, is moved in a Y axial direction by the Y-axis stepping motor 21b, is moved in a Z axial direction by the Z-axis stepping motor 21c, and is rotatably moved around a center axis that extends in a vertical direction (the Z axial direction) at the center of the XYZ stage 21 by the θ-axis stepping motor 21d.

(2) Product Having the Microneedle Array

The product having the microneedle array manufactured using the microneedle-array manufacturing apparatus 1 will now be explained. What is formed by the microneedle-array manufacturing apparatus 1 is a microneedle array 110, which comprises a plurality of microneedles 103 shown in FIG. 3.

The size of each microneedle 103 is set to, for example, a height in the range of from 10 μm to 1 mm, a bottom-surface maximum width in the range of 10 μm to 1 mm, and an aspect ratio in the range of from 0.5 to 4.

In addition, a spacing dl between mutually adjacent microneedles 103 (the distance to the most proximate location on a surface 102) is set to, for example, a range of from 10 μm to 2 mm. In terms of the density of the microneedles 103 that constitute the microneedle array 110, the number per square centimeter is set to, for example, a range of approximately from several to $10^5$. To manufacture the microneedle array 110 of this kind, the microneedle-array manufacturing apparatus 1 is configured such that it can repetitively move a distance of less than the spacing dl of the microneedles 103. In addition, the error in the movement distance of the microneedle-array manufacturing apparatus 1 is set such that it is smaller than the maximum width of the bottom surface of each microneedle 103.

The microneedle array 110 is fixed to the surface 102 of a plate-shaped base member 101. The external dimensions of the base member 101 are, for example, approximately 2 mm×17 mm×17 mm in size. To fix the microneedle array 110 to the surface 102, a laminated film 109 having a composition the same as that of bottom-part layers 105 is formed on the surface 102 of the base member 101. Thus, the microneedle array 110 is fixed to the base member 101, and thereby a product 100 having the microneedle array is formed. When tip parts of the microneedles 103 are sharpened, the angle in a cross section of each tip part in the vertical direction is, for example, 30°. Thus, when the tip part of each microneedle 103 is being sharpened, a wall of a recessed part 81 (refer to FIG. 8) on which the droplets land is tilted, and therefore it becomes easy to form each recessed part 81 into a shape that is suited to being filled by the droplets. Here, the droplets landing on the recessed part 81 refers to the striking and adhering of the droplets to the wall surface of the recessed part 81.

The plate-shaped base member 101 is a base member having good air permeability, for example, a porous-base member. For example, a porous-base member wherein cellulose acetate is the main component, a porous-ceramic-base member, a porous-metal-base member, a pulp-molded product wherein pulp is formed into a plate shape, or a porous-resin-base member can be used as the porous-base member.

Figure 3:
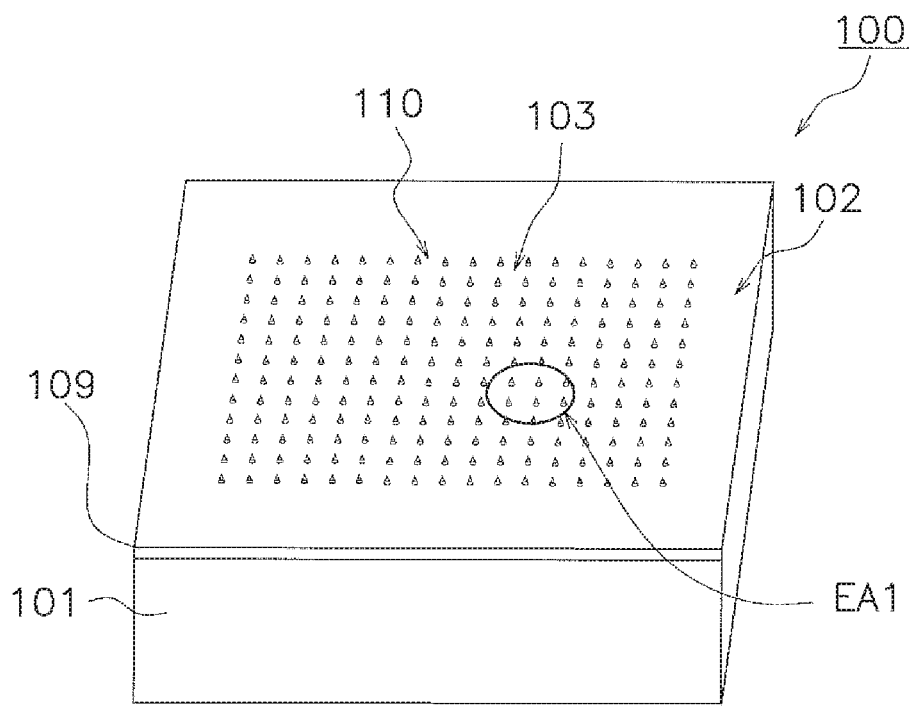
FIG. 3 is an oblique view that shows one example of a product having the microneedle array of the first embodiment.
Figure 4:
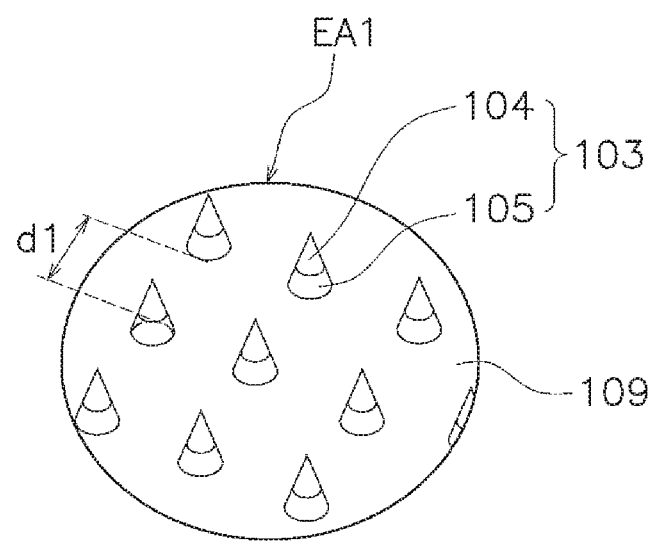
FIG. 4 is a partial-enlarged oblique view in which a part of FIG. 3 is enlarged.

In FIG. 4, a partial area EA1 in FIG. 3 is shown enlarged. Each microneedle 103 has a two-layer structure consisting of a peak-part layer 104 at the tip and the bottom-part layer 105 continuous therewith. The peak-part layer 104 and the bottom-part layer 105 have differing compositions.

In the explanation below, when speaking of the components of the raw-material liquid, those components are not necessarily dissolved in the raw-material liquid; for example, it also includes the case in which, for example, when the raw-material liquid is a suspension, the components of that suspension are, for example, in the form of microcapsules or liposomes.

(3) Mold

Figure 5:
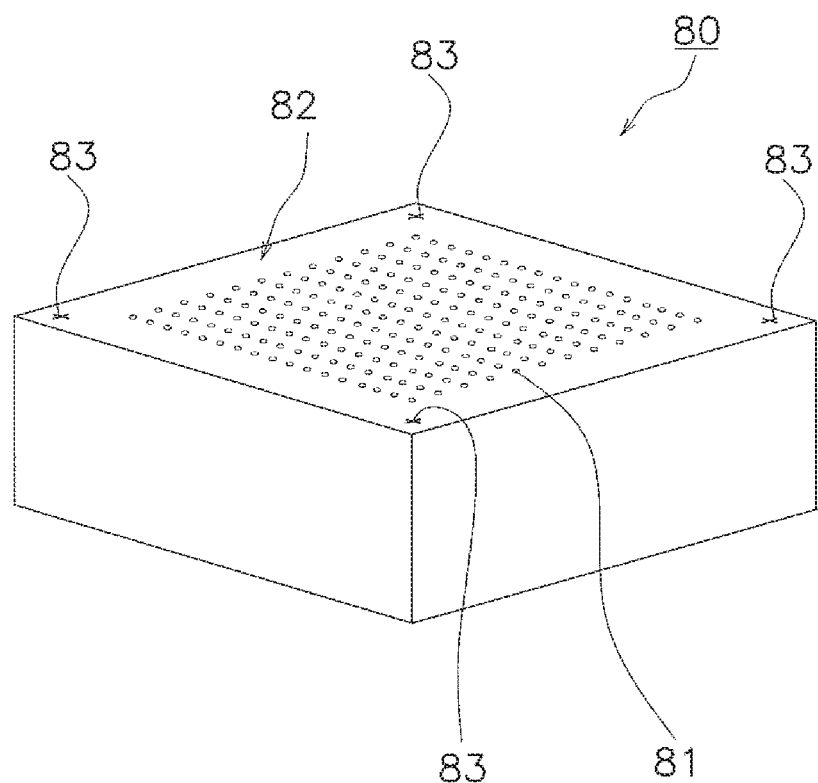
FIG. 5 is an oblique view that shows one example of a mold of the first embodiment.

The mold 80 shown in FIG. 5 should be formed of a hygienic material that is not attacked by the raw-material liquid and preferably is a material having high gas permeability. For example, it can be formed of a plastic, an elastomer, a ceramic, or a metal. The material with which the mold 80 is formed is preferably a silicone rubber. In addition, for example, polymethylpentene (TPX™) or polytetrafluoroethylene are preferable examples of a plastic with which the mold 80 is formed. In addition, stainless steel is a preferable example of a metal with which the mold 80 may be formed, because stainless steel having no gas permeability tends not to rust. The shape of each recessed part 81 of the mold 80 in a horizontal section along a surface 82 of the mold 80 is, for example, circular, polygonal, or elliptical. Furthermore, the internal space of each recessed part 81 is, for example, a space having a conical shape, a pyramidal shape, a columnar shape, or a prismatic shape.

Alignment marks 83 are formed on the surface 82 of the mold 80. The alignment marks 83 are read by the CCD camera 22 of the microneedle-array manufacturing apparatus 1. Control is performed such that, using the alignment marks 83 as a reference, the droplets delivered from the droplet-delivery apparatus 10 land inside the recessed parts 81, and therefore the position of each recessed part 81 is determined using the alignment marks 83 as a reference. Furthermore, the alignment marks 83 are hygienic and are formed of, for example, unevenness in the surface 82.

For the case in which the mold 80 is formed of a silicone rubber, the external dimensions of the mold 80 are, for example, 6 mm×20 mm×20 mm, and the size of the area in which the recessed parts 81 are formed is, for example, 15 mm×15 mm.

(4) Raw-Material Liquid

A peak-part-layer, raw-material liquid 91 (refer to FIG. 7) for forming the peak-part layers 104 of the microneedles 103 is, for example: a solution into which a solid raw material is dissolved into water, a mixed solvent of water and alcohol, or some other solvent; a suspension in which a solid raw material is dispersed in water, a mixed solvent of water and alcohol, or some other solvent; or a liquid mixture thereof. The solid raw material is a macromolecular substance that is nontoxic to the human body and includes, for example, resins that are nontoxic to the human body, polysaccharides that are nontoxic to the human body, proteins that are nontoxic to the human body, and compounds derived therefrom that are nontoxic to the human body. For example, bioactive substances used for the purpose of treating, diagnosing, or preventing injury or illnesses can be given as examples of compounds for being introduced to the human body.

A peak-part-layer, raw-material liquid is, for example, a liquid in which a bioactive substance, which is to be administered for the diagnosis, treatment, prevention, or the like of a disease, is added to a solvent, into which water soluble polysaccharides (including derivatives and salts thereof) have been dissolved. The solvent of such a peak-part-layer, raw-material liquid is evaporated, and thereby the peak-part layers 104, which contain the bioactive substance in a polysaccharides base material, are formed. Examples of water soluble polysaccharides (including derivatives and salts thereof) are sodium chondroitin sulfate, hyaluronate, dextran, and carboxymethyl cellulose. In addition, examples of such a bioactive substance are insulin and growth hormone.

In a bottom-part-layer, raw-material liquid for forming the bottom-part layers 105 of the microneedles 103, at least one constituent among the solid raw material and the solvent differs from that of the peak-part-layer, raw-material liquid. By making the constituents of the peak-part-layer, raw-material liquid and the bottom-part-layer, raw-material liquid different in this manner, the constituents of the peak-part layers 104 and the bottom-part layers 105 of the microneedles 103 are made different. The present embodiment explains, as an example of a case in which the microneedles 103 are used for medical care, a configuration in which an efficacious bioactive substance is included in the peak-part layers 104 but is not included in the bottom-part layers 105. However, for example, if the microneedles 103 are used for medical care, then the efficacious bioactive substance may be included in both the peak-part layers 104 and the bottom-part layers 105, and a configuration is also possible such that the type, the content, or the like of the bioactive substance included in the peak-part layers 104 and the type, the content, or the like of the bioactive substance included in the bottom-part layers 105 are made different, and thereby the efficacy, the efficacy duration, or the like produced by the peak-part layers 104 and the efficacy, the efficacy duration, or the like produced by the bottom-part layers vary. If the product 100 having the microneedle arrays is used for medical care, then by making the microneedles 103 with a two-layer structure in this manner, it becomes easy to handle a variety of dosage administrations.

The peak-part-layer, raw-material liquid is delivered, for example, as droplets from the droplet-delivery apparatus 10, and the droplet amount is set to a range of, for example, from 0.1 nL/droplet to 1 µL/droplet. For example, if the capacity of the recessed part 81 for forming one microneedle 103 is 20 nL and if it is given that one recessed part 81 is filled by 20 droplets, then one droplet is 1 nL. To perform filling with such minute droplets, the viscosity is preferably low, for example, the viscosity is set to a range of from 0.1 mPa·sec to 100 mPa·sec and more preferably is set to a range of from 1 mPa·sec to 10 mPa·sec.

(5) Method of Manufacturing the Product Having the Microneedle Array

Figure 6:
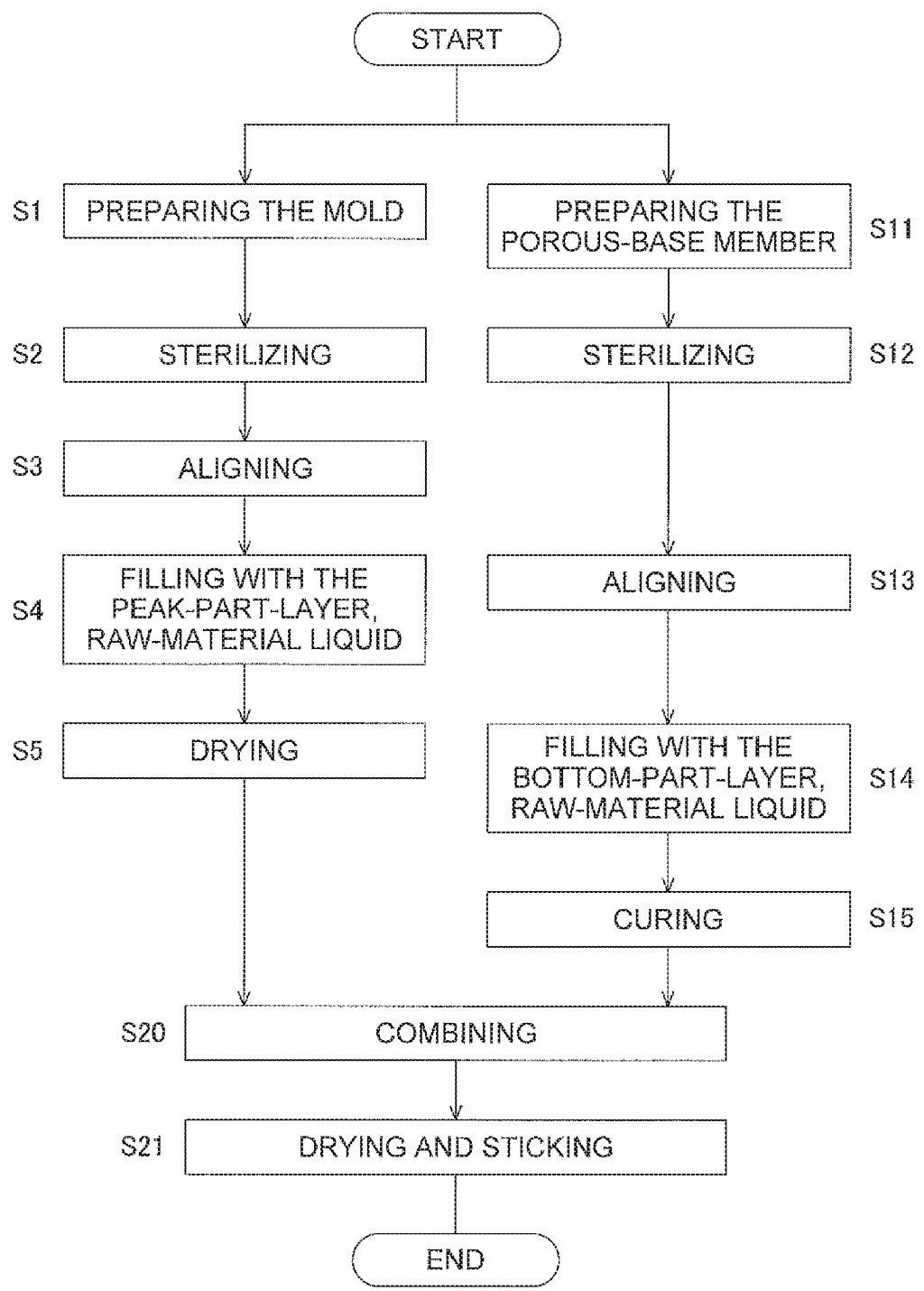
FIG. 6 is a flow chart that depicts one example of a microneedle-array manufacturing method of the first embodiment.

FIG. 6 is a flow chart for explaining the step of manufacturing the product 100 having the microneedle array described above using the microneedle-array manufacturing apparatus 1. In this step of manufacturing the product 100 having the microneedle array, the procedure from a step S1 to a step S5 and the procedure from a step S11 to a step S15 in FIG. 6 can be performed independently or in parallel. However, in the flow of the two procedures, procedures that can be standardized may be standardized. In addition, the operation of the microneedle-array manufacturing apparatus 1 in each step is controlled by the control apparatus 30; however, in the explanation below, references regarding the control of each part of the microneedle-array manufacturing apparatus 1 by the control apparatus 30 may be partly omitted. Furthermore, in the first embodiment, only the first delivery-head actuator 12*a*, which delivers droplets from the nozzle 11*a*, is used, and the explanation regarding a manufacturing method that uses the second delivery-head actuator 12b is given in a second embodiment. In addition, in the first embodiment, the θ-axis stepping motor 21d is not used, and the explanation regarding a manufacturing method that uses the θ-axis stepping motor 21d is given in a third embodiment.

The step S1 to the step S5 in FIG. 6 is the procedure that uses the mold 80. First, the mold 80 shown in FIG. 5 is prepared (the step S1). The mold 80 preparing step of the step S1 is performed by, for example, washing a prescribed number of the molds 80 and lining them up at a prescribed location. All of the prepared molds 80 are sterilized (the step S2) using, for example, an autoclave (not shown). In a clean environment, the sterilized mold 80 is mounted on the XYZ stage 21 of the microneedle-array manufacturing apparatus 1, and then alignment is performed (the step S3).

The alignment of the sterilized mold 80 is performed after the mold 80 is mounted on the XYZ stage 21 by, for example, a sterilized robot arm or the like. Alignment is performed by the CCD camera 22 taking images of the alignment marks 83 on the mold 80 on the XYZ stage 21 and by the control apparatus 30 performing recognition using the alignment marks 83 as a reference. By virtue of the position of each recessed part 81 being identified in the control apparatus 30 based on the alignment marks 83 of the mold 80, it becomes possible for the XYZ stage 21 to move the mold 80 relative to the nozzle 11a of the droplet-delivery apparatus 10 such that the nozzle 11a of the droplet-delivery apparatus 10 correspondingly moves to the adjacent recessed part 81 in sequence in the manner of a single-stroke drawing.

Figure 7:
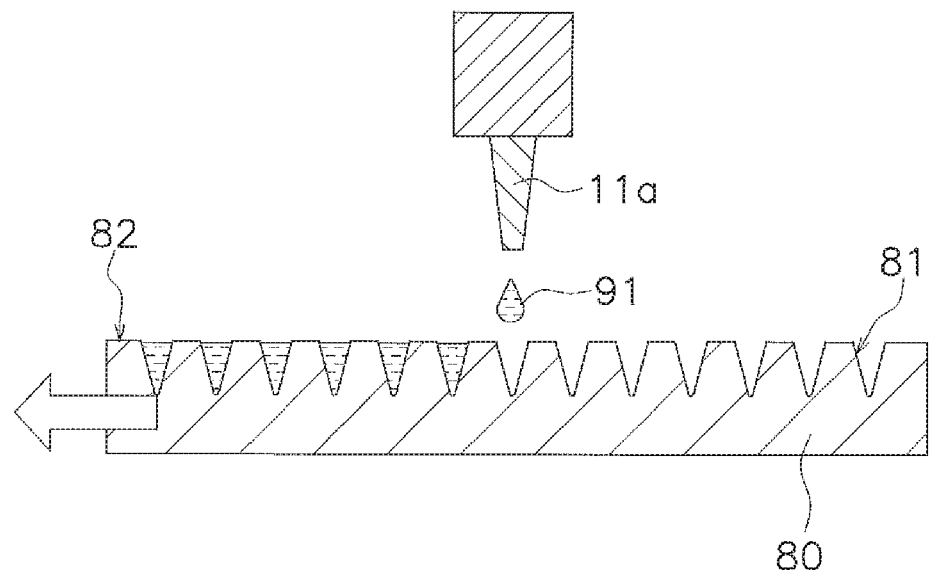
FIG. 7 is a schematic cross-sectional view for explaining the delivery of a droplet to a recessed part.
Figure 8:
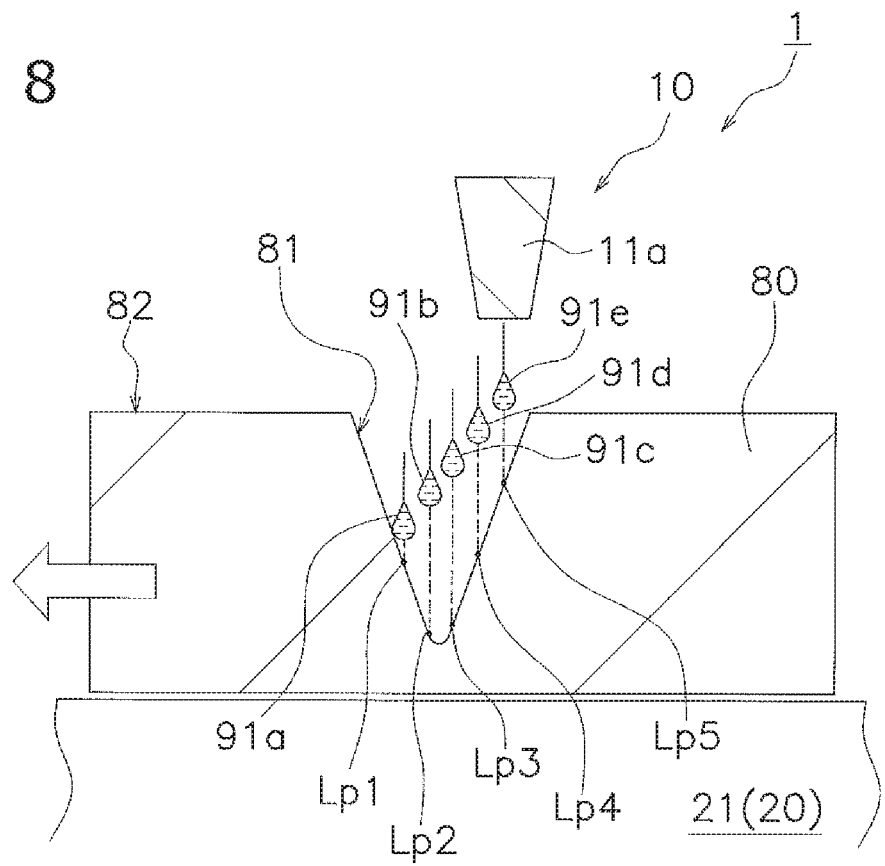
FIG. 8 is a schematic, enlarged cross-sectional view for explaining the landing of droplets in a recessed part.

In the step S4, as shown in FIG. 7 and FIG. 8, the mold 80 is caused to move with respect to the nozzle 11a, and droplets delivered from the nozzle 11a are caused to directly land on each recessed part 81 of the mold 80; thereby, each recessed part 81 is filled with the peak-part-layer, raw-material liquid 91. As shown in FIG. 8, if the droplet that lands in each recessed part 81 is subdivided, then the amount of the peak-part-layer, raw-material liquid 91 that makes contact with the air increases, and thereby the drying time of the peak-part-layer, raw-material liquid 91 can be shortened. To ensure that the peak-part-layer, raw-material liquid 91 delivered from the nozzle 11a does not land on the surface 82 of the mold 80, control is performed such that the droplet-delivery apparatus 10 and the XYZ stage 21 operate synchronously. FIG. 8 shows five droplets 91a, 91b, 91c, 91d, 91e of the peak-part-layer, raw-material liquid 91 delivered from the nozzle 11a to one of the recessed parts 81, and shows corresponding landing points Lp1, Lp2, Lp3, Lp4, Lp5 of the droplets 91a, 91b, 91c, 91d, 91e. The landing points Lp1, Lp2, Lp3, Lp4, Lp5 are mutually differing positions within each recessed part 81. For example, the landing points Lp1, Lp2, Lp3, Lp4, Lp5 can be varied by successively delivering droplets while the nozzle 11a is moved relative to the mold 80 at a constant velocity. Thus, if delivery is performed repetitively while the nozzle 11a is moved and the droplets are caused to land at differing positions, then the filling time of each mold 80 can be shortened and, in turn, the product having the microneedle array can be manufactured in a short time. In addition, the interval from when landing starts until landing ends in each recessed part 81 may be set such that the relative velocity of the nozzle 11a with respect to the mold 80 is varied.

The number of droplets of the peak-part-layer, raw-material liquid 91 to be delivered is not limited to five and can be set as appropriate. The number of droplets per single recessed part 81 is set to a range of, for example, from one droplet to several tens of droplets. In addition, the liquid-droplet amount of the peak-part-layer, raw-material liquid 91 to be delivered can also be set as appropriate. For example, the amounts of the droplets 91a, 91b, 91c, 91d, 91e can also be set such that they are fixed and can also be set such that they differ from one another. There is, for example: a setting in which the liquid-droplet amount is decreased the closer it gets to the end of each recessed part 81 and is increased the closer it gets to the center part; a setting in which, conversely, the liquid-droplet amount is increased the closer it gets to the end of each recessed part 81 and is decreased the closer it gets to the center part; a setting in which the liquid-droplet amount is decreased as the end of the delivery approaches more than when the delivery starts in each recessed part 81; and a setting in which, conversely, the liquid-droplet amount is increased as the end of the delivery approaches more than when the delivery starts in each recessed part 81.

In addition, here, the total of the liquid-droplet amounts of the five droplets of the peak-part-layer, raw-material liquid 91 delivered to one recessed part 81 is set such that it is equal to the volume of the internal space of that recessed part 81 (the capacity of the recessed part 81). Accordingly, when the peak-part-layer, raw-material-liquid filling step of the step S4 ends, all the recessed parts 81 are fully filled with the peak-part-layer, raw-material liquid 91. However, the fill amount of the peak-part-layer, raw-material liquid 91 in one mold 80 can also be set such that it is varied in accordance with the positions of the recessed parts 81. For example, there is a setting in which the fill amount of the peak-part-layer, raw-material liquid 91 in the recessed parts 81 is increased near the center part of the mold 80 and is decreased as it approaches an end part of the mold 80, and there is a setting in which, conversely, the fill amount of the recessed parts 81 is increased near the center part of the mold 80 and the fill amount is decreased as it approaches the end part of the mold 80. To vary the fill amount, for example, the liquid-droplet amount of one droplet may be varied, the number of droplets per recessed part 81 may be varied, or both the liquid-droplet amount and the number of droplets may be varied.

The relative movement of the nozzle 11a with respect to the recessed parts 81 is principally movement in the XY coordinates of the XYZ stage 21, that is, in the in-plane directions of the surface 82 of the mold 80, but that relative movement may be combined with movement in the Z axial direction. For example, if the size of the recessed parts 81 of the mold 80 varies by location, then, to modify the landing accuracy, the nozzle 11a may be brought toward or away from the mold 80.

When the peak-part-layer, raw-material-liquid filling step (the step S4) ends, the mold 80 is moved from the XYZ stage 21 to an air-drying part (not shown) by, for example, the sterilized robot arm or the like. In this air-drying part, for example, the molds 80 for which filling has completed are successively loaded on a belt conveyor (not shown) and then moved under a draft of clean dry air. Furthermore, at the end point of the belt conveyor, in the state in which the peak-part-layer, raw-material liquid 91 has dried and solidified, the molds 80 are successively removed and moved to the next step, which is the combining step.

Figure 9A:
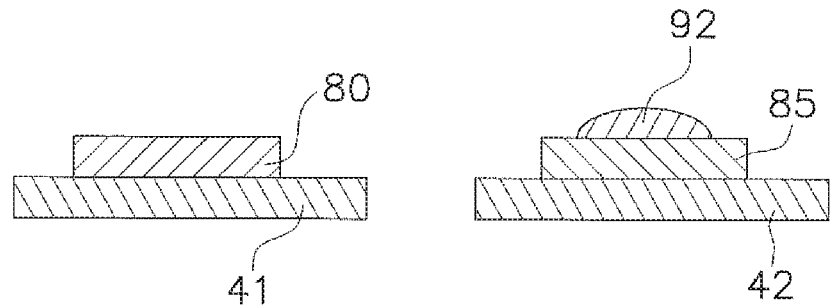
FIG. 9A is a schematic cross-sectional view that shows the state prior to assembly in an assembling process.

The procedure of step S11 to step S15, which is performed in parallel with the procedure of step S1 to step S5 described above, is a procedure that is performed using a porous-base member 85 (refer to FIG. 9A). First, in a step of preparing the porous-base member 85, the surfaces of a prescribed number of porous-base members 85 are cleaned by, for example, air, and then lined up at a prescribed location. All the prepared porous-base members 85 are sterilized using, for example, an autoclave (not shown) (step S12). The sterilized porous-base members 85 are sequentially aligned by a feeder apparatus (not shown) with respect to a dispenser (not shown) located in a dispenser part (step S13).

In the step S14, a bottom-part-layer, raw-material liquid 92 is distributed by the dispenser to the porous-base member 85 and, as shown in FIG. 9A, is placed on the porous-base member 85 such that the bottom-part-layer, raw-material liquid 92 makes contact with the porous-base member 85. With regard to the bottom-part-layer, raw-material liquid 92, for example, the viscosity is set to a range of 1 Pa-sec or greater and 1000 Pa-sec or less, and, if the mold 80 is 20 mm×20 mm in size, then the amount is set to several tens of milligrams. Because the bottom-part-layer, raw-material liquid 92 is also the material that, based on the method described below, constitutes the laminated film 109, the bottom-part-layer, raw-material liquid 92 preferably has a comparatively high viscosity as described above. To cause the bottom-part-layer, raw-material liquid 92, which has such a comparatively high viscosity, to take to the porous-base member 85, the manufacturing method does not proceed to the drying-and-sticking step (the step S20) immediately after the bottom-part-layer, raw-material liquid 92 has been filled. A curing step (the step S15) is provided for creating the time needed for the bottom-part-layer, raw-material liquid 92 to penetrate the porous-base member 85 by capillary action or the like. In the curing step, it is just left as is for an appropriate time within a range of, for example, from several to several tens of seconds. In the curing step, for example, a penetration-promoting means may be applied, such as applying vibration, high pressure, or the like in the state in which the bottom-part-layer, raw-material liquid 92 is in contact with the porous-base member 85.

In the subsequent combining step (the step S20), as shown in FIG. 9A, the mold 80 is fixed to a sucking stage 41 by sucking. In addition, the porous-base member 85 is mounted on a mounting stage 42. Consequently, the mold 80, which underwent the drying step (the step S5) is placed on the sucking stage 41 by, for example, a sterilized robot arm, and the porous-base member 85, which underwent the curing step (the step S15), is mounted on the mounting stage 42 by, for example, the sterilized robot arm.

Figure 9B:
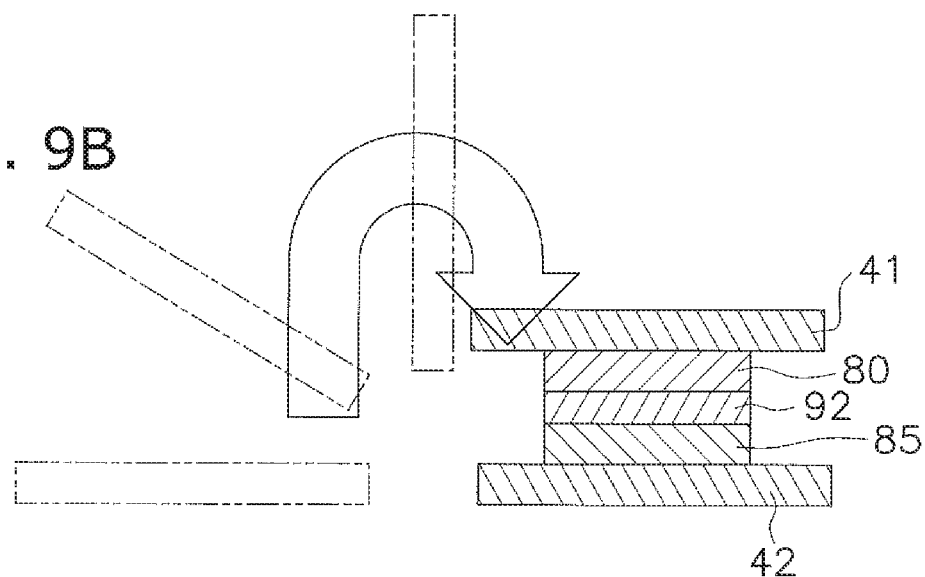
FIG. 9B is a schematic cross-sectional view that shows the state during assembly in the assembling process.
Figure 9C:
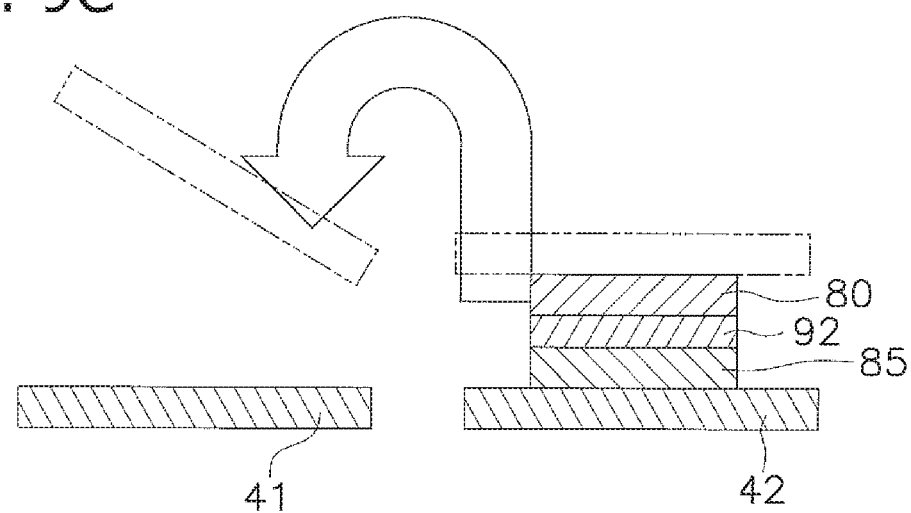
FIG. 9C is a schematic cross-sectional view that shows the state in which assembly has been completed in the assembling process.

Next, as shown in FIG. 9B, the sucking stage 41 is lifted up and turned upside down such that the mold 80, which is fixed to the sucking stage 41, overlays the porous-base member 85, which is placed on the mounting stage 42. As shown in FIG. 9B, in the state in which the mold 80 overlays the porous-base member 85, the sucking stage 41 pushes against the mounting stage 42 and thereby applies a prescribed pressure. Owing to this prescribed pressure, the bottom-part-layer, raw-material liquid 92 interposed between the porous-base member 85 and the mold 80 spreads. However, the applied pressure is adjusted to a prescribed pressure such that the bottom-part-layer, raw-material liquid 92 does not spread excessively and get pressed out from the porous-base member 85. To obtain such a result, for example, a suitable value for the prescribed pressure is investigated by performing a preliminary experiment. When pressure is applied to the mold 80 by the sucking stage 41, the fixing of the mold 80 to the sucking stage 41 may be maintained as is or the fixing may be released. Next, as shown in FIG. 9C, in the state in which the fixing of the sucking stage 41 to the mold 80 has been released, the sucking stage 41 is removed from the mold 80. Furthermore, the volume of the peak-part-layer, raw-material liquid 91 is reduced by the drying, and thereby level differences are created between the surface 82 of the mold 80 and the surfaces of the substance that was produced by the solidification of the peak-part-layer, raw-material liquid 91. The bottom-part-layer, raw-material liquid 92 penetrates the spaces inside the recessed parts 81 created by these level differences, and thereby the bottom-part layers 105 of the microneedles 103 can be formed.

The mold 80 and the porous-base member 85 in the state shown in FIG. 9C are moved from the mounting stage 42 to a stack part (not shown). At the stack part, in the state in which a load is applied to the mold 80 from above, the bottom-part-layer, raw-material liquid 92 between the mold 80 and porous-base member 85 is dried. Methods of applying the load to the mold 80 from above include, for example, a method in which a weight is placed on the mold 80 and a method in which an assembly of the mold 80 and the porous-base member 85 is set in a load-stacking special-purpose machine, which applies a load by pressure using air pressure, a spring, or the like.

(6) Modified Examples (6-1) Modified Example 1A

The abovementioned first embodiment explained the microneedles 103 having a two-layer structure, wherein the peak-part layers 104 contain the bioactive substance and therefore are efficacious, but the bottom-part layers 105 do not contain the bioactive substance and therefore are not efficacious. For example, if it is desired to maximally reduce the manufacturing error in the amount of the pharmaceutical agent included in the peak-part layers 104, then it becomes necessary to control, with extremely good accuracy, the amount of the raw-material liquid with which the recessed parts are filled. In such a case, compared with using a squeegee to fill the recessed parts with the raw-material liquid as in the conventional case, the microneedle-array manufacturing apparatus 1, the microneedle-array manufacturing method, and the like according to the first embodiment described above can adjust the amount of the pharmaceutical agent with extremely good accuracy because filling the recessed parts with the raw-material liquid using a prescribed number of droplets wherein the liquid amount is regulated makes it possible to control the amount of the raw-material liquid with better accuracy.

However, the microneedle-array manufacturing apparatus 1, the microneedle array manufactured by the microneedle-array manufacturing method, and the like explained in the first embodiment are not limited to the microneedle array 110 comprising the microneedles 103 having a two-layer structure as described above. For example, it is also possible to manufacture a microneedle array comprising microneedles having a two-layer structure wherein the peak-part layers 104 do not contain the bioactive substance and therefore are not efficacious, and the bottom-part layers 105 do contain the bioactive substance and therefore are efficacious. In addition, as explained in (4) Raw-Material Liquid above, the efficacious bioactive substance may be included in both the peak-part layer and the bottom-part layer of each microneedle. Furthermore, it is also possible to manufacture a microneedle array comprising the microneedles having a multilayer structure of more than two layers, that is, three or more layers. Thus, the microneedle-array manufacturing apparatus 1, the microneedle-array manufacturing method, and the like explained in the first embodiment are suited to the manufacture of a product having the microneedle array comprising a plurality of the microneedles, wherein the compositions of the multiple layers differ from one another.

In addition, if the field in which the microneedle array is used is a field outside of medical care, for example, a field related to beauty or health, then it may be that the microneedles 103 have a two-layer structure in which both the peak-part layers 104 and the bottom-part layers 105 do not contain the bioactive substance and therefore are not efficacious.

In addition, at least one among the peak-part layers 104 and the bottom-part layers 105 can also be formed of the bioactive substance alone, without using polysaccharides as exemplified in the first embodiment.

The peak-part-layer, raw-material liquid described above may be, for example, a solution wherein is dissolved at least one or a combination of the above-discussed water-soluble polysaccharides, a water-soluble protein, polyvinyl alcohol, a carboxyvinyl polymer, and sodium polyacrylate. Serum albumin is an example of a water-soluble protein. In addition, the peak-part-layer, raw-material liquid may contain other substances, for example, monosaccharides, oligosaccharides, or the like. Glucose can be given as an example of a monosaccharide, disaccharides can be given as an example of oligosaccharides, and sucrose is an example of a disaccharide.

(6-2) Modified Example 1B

In the abovementioned first embodiment, alignment is performed by taking images of the alignment mark 83 with the CCD camera 22 and moving the XYZ stage 21 using the alignment marks 83 as a reference, but the aligning method is not limited to such a method; for example, alignment may be performed by striking a side surface of the mold 80 with a jig to establish a reference position.

(6-3) Modified Example 1C

Figure 17A:
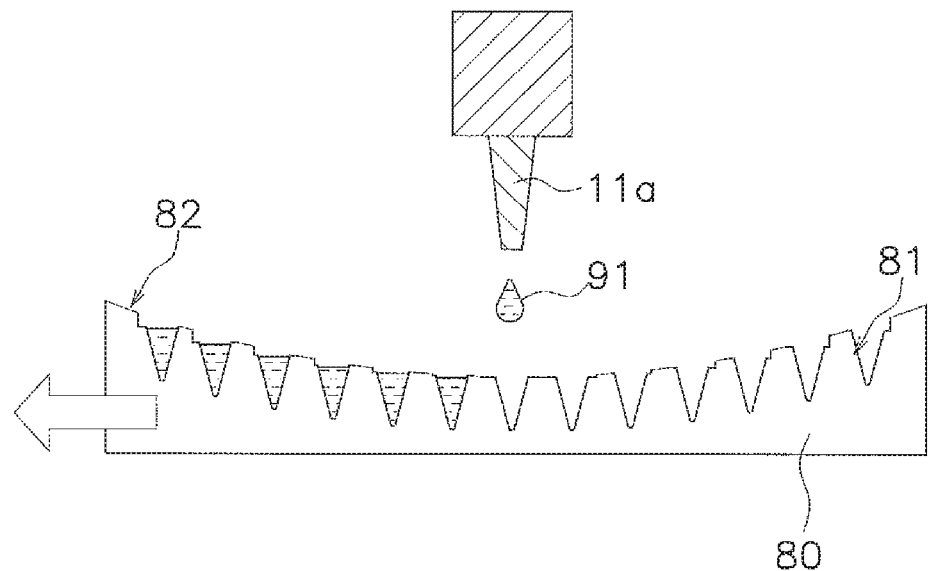
FIG. 17A is a schematic cross-sectional view for explaining the microneedle-array manufacturing method according to a modified example 1C.
Figure 17B:
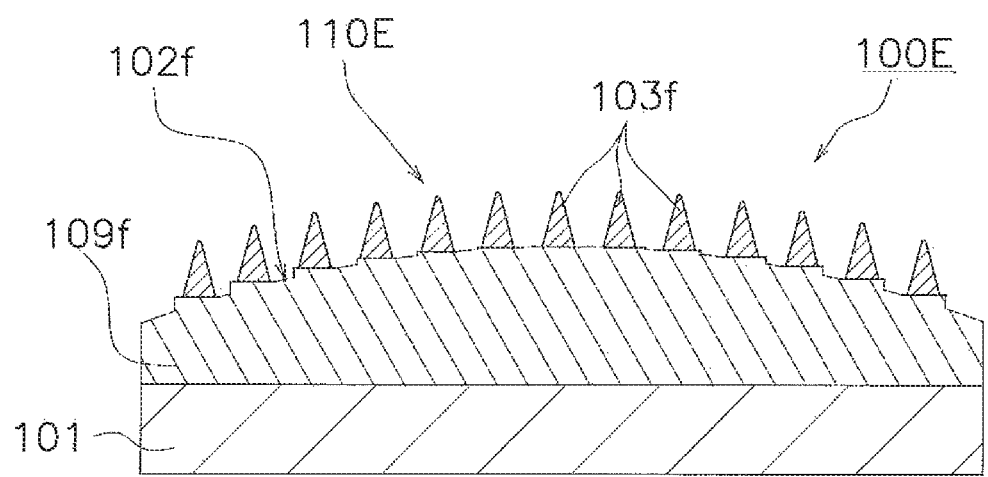
FIG. 17B is a conceptual diagram for explaining one example of a product having the microneedle array according to the modified example 1C.
Figure 18A:
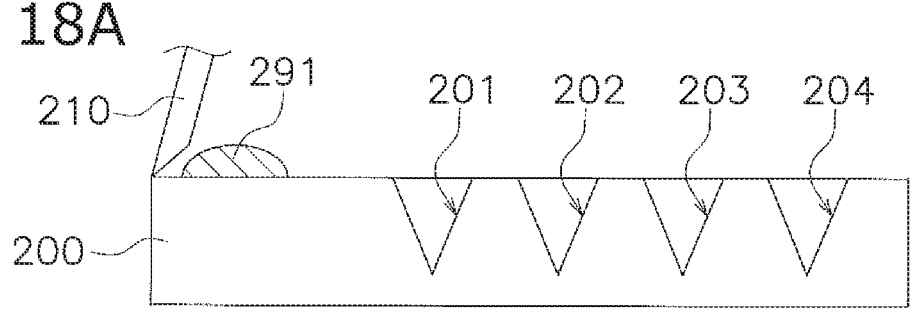
FIG. 18A is a schematic cross-sectional view for explaining a conventional microneedle-array manufacturing method.
Figure 18B:
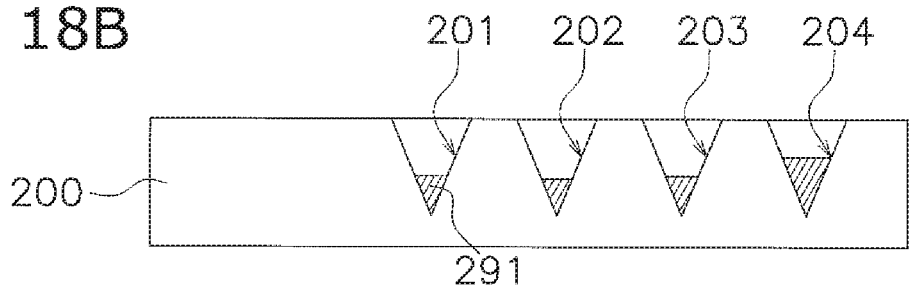
FIG. 18B is a schematic cross-sectional view that shows one manufacturing step of a conventional microneedle array.
Figure 18C:
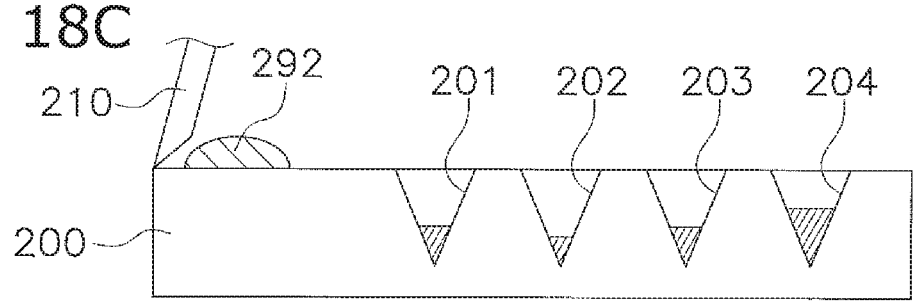
FIG. 18C is a schematic cross-sectional view of a conventional mold in which peak-part layers have been formed.
Figure 18D:
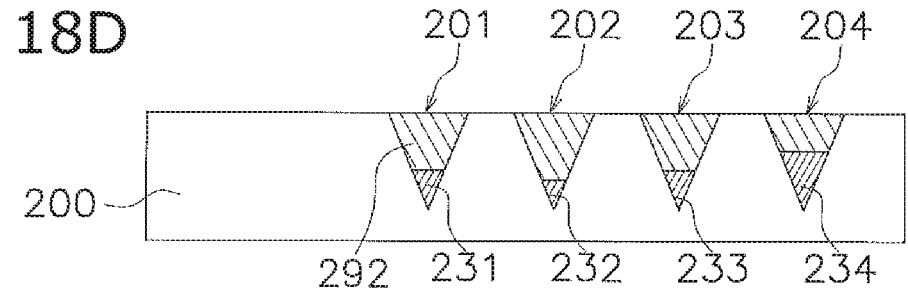
FIG. 18D is a schematic cross-sectional view for explaining a step of filling the conventional microneedle array.
Figure 18E:
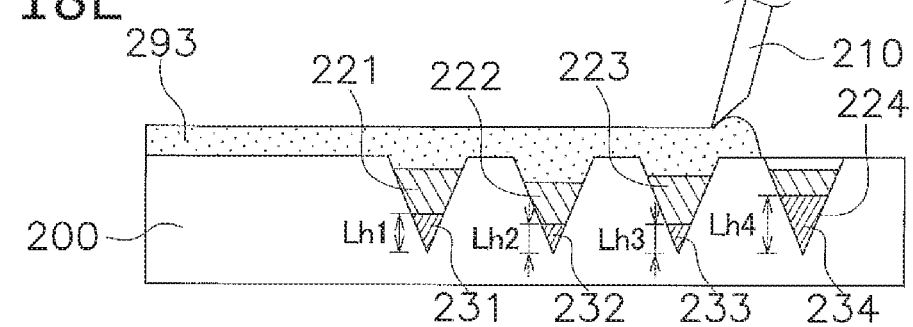
FIG. 18E is a schematic cross-sectional view that shows a step of fixing a conventional microneedle array.

The abovementioned first embodiment explained an exemplary case in which the base member 101 has a flat plate shape; however, the base member 101 may have a thin sheet shape or its front surface may have a curved three-dimensional shape. As shown in FIG. 17A, a surface 82 of a mold 80 is made into a curved shape as in a concave mirror, and the recessed parts 81 can be filled with the peak-part-layer, raw-material liquid 91 by moving the nozzle 11a along the curved surface of the surface 82. As shown in FIG. 17B, if formed in this manner, multiple microneedles 103f can be formed continuously and parallel to one another regardless of the curved-surface shape of a surface 102f of a fixed part 109f. Thereby, it becomes easy for the microneedle 103f at any location of a microneedle array 110E to stick. For example, if the microneedle array is formed on a sheet and that sheet is three-dimensionally deformed, then the microneedles become substantially normal with respect to the curved surface and are not parallel to one another, and therefore some of the microneedles tend not to stick, tend to break, or the like.

In addition, the fixed part 109f can be formed by the same method as in the first embodiment using the bottom-part-layer, raw-material liquid 92. Based on the number of droplets of the peak-part-layer, raw-material liquid 91, the amount of the composition included per single microneedle 103f can be adjusted with good accuracy to a preset amount.

Furthermore, the contour of the fixed part 109f may be some other shape, as long as it is a three-dimensional shape. In addition, if the plurality of microneedles 103f is three-dimensionally disposed on the surface 102f of the fixed part 109f and the microneedles 103f are formed parallel to one another, then the functions and effects described above will be exhibited.

For example, the contour of the fixed part can also be indented on the side opposite the side on which the microneedles project. Thus, if the contour of the fixed part is made curved as in a concave mirror and if this curved surface is made such that it continues across the plurality of microneedles, then the microneedles tend to conform to the skin in cases in which the skin gradually swells. If the microneedle array is configured in this manner, then it becomes easy for the microneedles to be inserted to their roots, because the boundary between the microneedles and the fixed part is located at a place at which it conforms to the skin. Thus, the mold for forming the microneedle array, wherein the fixed part is curved as in a concave mirror, rises up at the center as in a convex mirror and has a contour that is symmetric with the mold 80A. It is possible to curve the surface of the fixed part into a gentle convex shape, using the vicinity of the center of the fixed part as the vertex, such that the surface gradually becomes low toward the perimetric edge of the fixed part; it is also conversely possible to curve the surface of the fixed part into a gentle concave shape, using the vicinity of the center of the fixed part as a bottom point, such that the surface gradually becomes high toward the perimetric edge of the fixed part. In addition, it is also possible to combine the concave curved surface and the convex curved surface. In FIG. 17B, the plurality of microneedles 103f are configured on the surface 102f of the fixed part 109f, which is one curved surface.

Furthermore, the fixed part 109f is formed by the same method as in the first embodiment using the bottom-part-layer, raw-material liquid 92, and therefore the fixed part 109f can be made water soluble. In addition, the microneedles 103f can be formed by the same method as in the first embodiment using the peak-part-layer, raw-material liquid 91, and therefore the microneedles 103f can be made water soluble. Furthermore, for example, the composition amounts of the microneedles 103f and the fixed part 109f can be made different. By making the composition amounts of the microneedles 103f and the fixed part 109f different, it is possible to make it such that the microneedles 103f contain the efficacious bioactive substance and such that the fixed part 109f does not contain the efficacious bioactive substance, and thereby to make it possible to form a microneedle array that fits the target to be stuck while economizing on the efficacious bioactive substance.

Second Embodiment (7) Overview of Microneedle-Array Manufacturing Method

The abovementioned first embodiment explained a case in which one nozzle 11a is used in the droplet-delivery apparatus 10, but a case in which the two nozzles 11a, 11b are used will now be explained as a second embodiment, as shown in FIG. 10. The two cartridges 13a, 13b shown in FIG. 10 contain peak-part-layer, raw-material liquids 91, 93, whose constituents differ.

In the droplet-delivery apparatus 10 shown in FIG. 10, droplets of the peak-part-layer, raw-material liquid 91 and droplets of the peak-part-layer, raw-material liquid 93 are alternately delivered by the nozzle 11a and the nozzle 11b to mutually adjacent recessed parts 81. In addition, the total liquid-droplet amounts delivered by the nozzles 11a, 11b per recessed part 81 differ.

Figure 11:
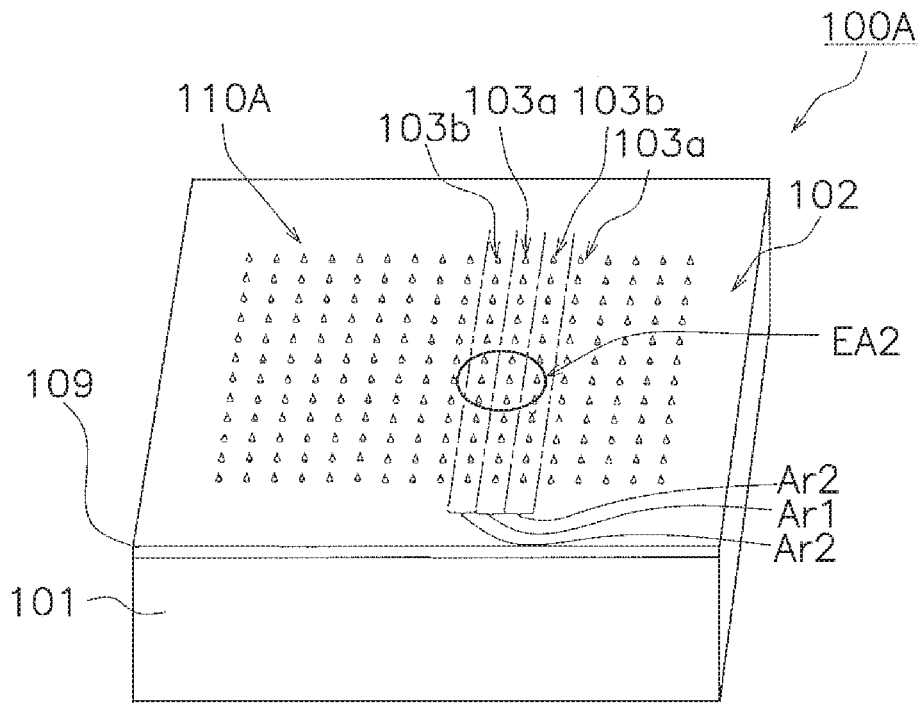
FIG. 11 is an oblique view that shows one example of a product having the microneedle array of the second embodiment.
Figure 12:
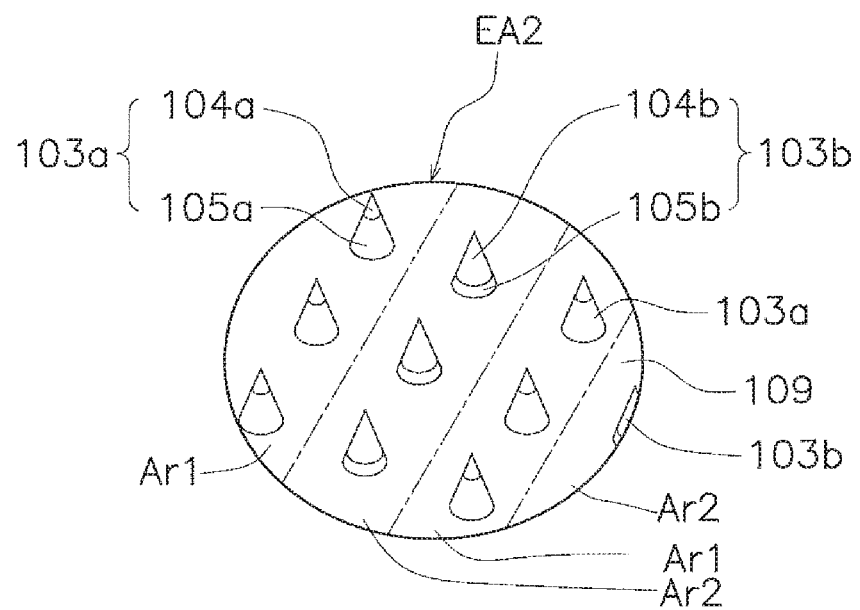
FIG. 12 is a partial, enlarged oblique view in which part of FIG. 11 is enlarged.

FIG. 11 shows a product 100A having a microneedle array 110A formed by the manufacturing method described above. FIG. 12 shows an enlargement of a partial area EA2 in FIG. 11. The same as in the microneedles 103 according to the first embodiment, both first microneedles 103a and second microneedles 103b according to the second embodiment have a two-layer structure comprising peak-part layers 104a, 104b at the tips and bottom-part layers 105a, 105b continuous therewith. Here, the bottom-part layers 105a, 105b are second layers that follow the peak-part layers 104a, 104b. The peak-part layers 104a and the bottom-part layers 105a of the first microneedles 103a differ from one another, and the peak-part layers 104b and the bottom-part layers 105b of the second microneedles 103b differ from one another. The bottom-part layers 105a, 105b are formed by the same method as in the first embodiment and are formed of the same component; however, because the layer thicknesses of the peak-part layers 104a, 104b differ, the layer thicknesses of the bottom-part layers 105a, 105b naturally differ from one another.

Here, the type of the (a third composition) of the bottom-part layers 105a of the first microneedles 103a differs from that of the composition (a first composition) of the peak-part layers 104a of the first microneedles 103a, and the type of the composition (a fourth composition) of the bottom-part layers 105b of the second microneedles 103b differs from that of the composition (a second composition) of the peak-part layers 104b of the second microneedles 103b. Furthermore, the type and the amount of the composition (the second composition) of the peak-part layers 104b of the second microneedles 103b differ from those of the composition (the first composition) of the peak-part layers 104a of the first microneedles 103a. Furthermore, in the case shown, the amount of the composition (the third composition) of the bottom-part layers 105a of the first microneedles 103a and the amount of the (the fourth composition) of the bottom-part layers 105b of the second microneedles 103b differ.

In FIG. 11 and FIG. 12, columns in which the first microneedles 103a are formed are first areas Ar1, and columns in which the second microneedles 103b are formed are second areas Ar2. The second areas Ar2 are disposed on both sides of each first area Ar1 such that the first area Ar1 is surrounded thereby. In this case, at the same time, the first areas Ar1 are also disposed on both sides of each second area Ar2 such that the second area Ar2 is surrounded thereby. That is, the plurality of first areas Ar1 and the plurality of second areas Ar2 are configured such that the first areas Ar1 and the second areas Ar2 are disposed alternately lined up.

In the conventional microneedle-array manufacturing method that uses a squeegee, the structure of the microneedles alternately differs by adjacent columns in this manner and, moreover, it is difficult to adjust the layer thicknesses of the microneedles with good accuracy; however, that becomes possible with the method of manufacturing the microneedle array 110A according to the second embodiment.

In the method of manufacturing the microneedle array 110A according to the second embodiment as described above, only the peak-part-layer, raw-material-liquid filling step (the step S4) shown in FIG. 6 is modified as described above, and other steps are performed the same as in the first embodiment.

(8) Modified Examples (8-1) Modified Example 2A

In the abovementioned second embodiment, the type of the third composition differs from that of the first composition, and the type of the fourth composition differs from that of the second composition. Furthermore, the type and the amount of the second composition differ from those of the first composition. The second embodiment describes an exemplary case in which, furthermore, the amounts of the third composition and the fourth composition differ; however, combinations like the following are also possible.

That is, configurations are also possible such that: the type of the third composition differs from that of the first composition and the type of the fourth composition differs from that of the second composition; the type and the amount of the second composition differ from those of the first composition; and both the third composition and the fourth composition differ.

For example, by putting the peak-part-layer, raw-material liquid 91 of the same composition into the cartridge 13a and the cartridge 13b, a configuration is possible such that the type of the third composition differs from that of the first composition and the type of the fourth composition differs from that of the second composition, only the amounts of the first composition and the second composition differ, and only the amounts of the third composition and the fourth composition differ.

(8-2) Modified Example 2B

The abovementioned second embodiment explains about columns of the first microneedles 103a disposed in straight lines and of the second microneedles 103b disposed in straight lines, as shown in FIG. 11 and FIG. 12. However, the layout of the microneedles having differing structures is not limited to the layout shown in FIG. 11 and FIG. 12. For example, an arbitrary number of columns of the first microneedles 103a and the second microneedles 103b may be alternately lined up, such as by lining up m1 columns (where m1 is a natural number) of the first microneedles 103a followed by n1 columns (where n1 is a natural number) of the second microneedles 103b followed by m2 columns (where m2 is a natural number) of the first microneedles 103a followed by n2 columns (where n2 is a natural number) of the second microneedles 103b. For example, the dosages of two types of pharmaceutical agents can be adjusted by adjusting the respective number of columns and thereby adjusting the ratio of the total volume of the peak-part layers 104a of the first microneedles 103a to the total volume of the peak-part layers 104b of the second microneedles 103b included in one microneedle array.

Figure 13:
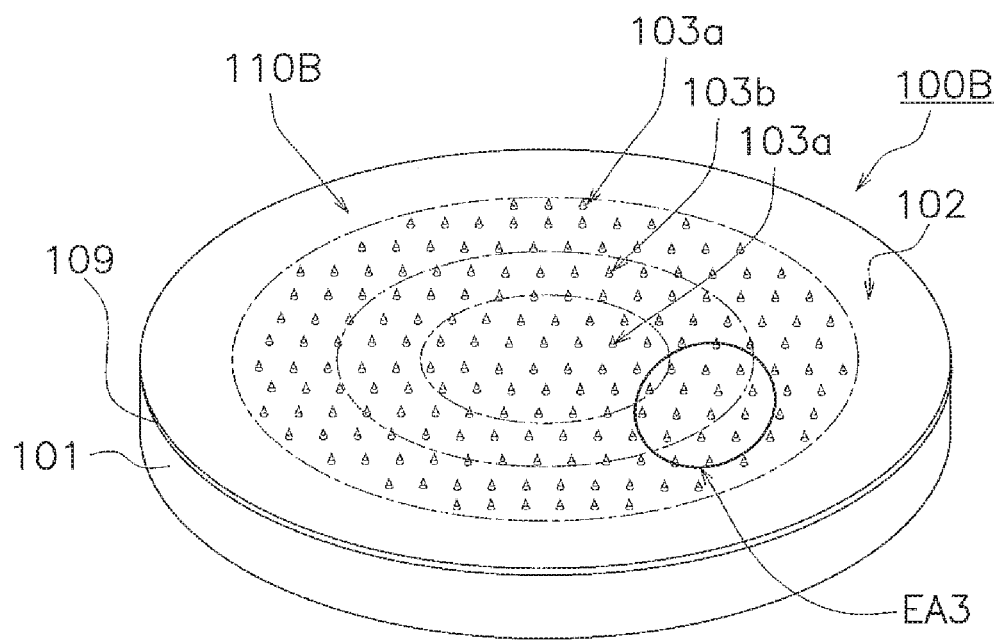
FIG. 13 is an oblique view that shows another example of a product having the microneedle array of the second embodiment.
Figure 14:
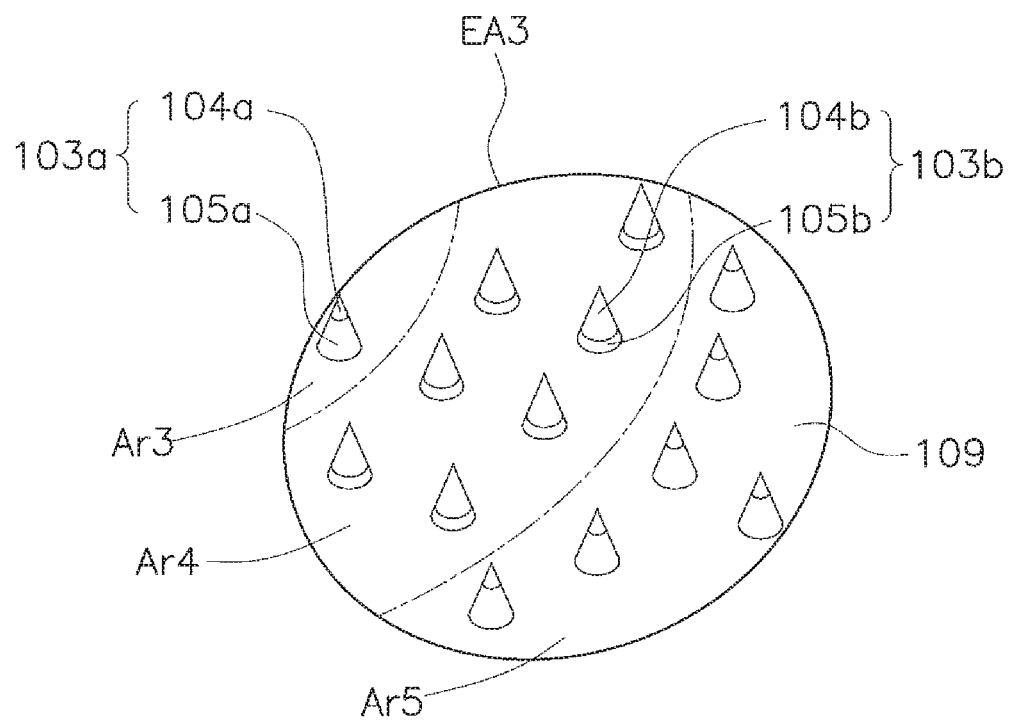
FIG. 14 is a partial, enlarged oblique view in which part EA3 of FIG. 13 is enlarged.

In addition, for example, on a product 100B as shown in FIG. 13 and FIG. 14, it is also possible to dispose columns of the first microneedles 103a in a circular-shaped first area Ar3 and a ring-shaped first area Ar5, and to dispose a second area Ar4, in which there are columns of the second microneedles 103b, such that it surrounds the columns of the first microneedles 103a in the first area Ar5. In addition, in this case, the first area Ar5 is disposed such that it surrounds the second area Ar4. In the case wherein a microneedle array 110B is disposed within a circle in this manner, if the microneedles 103a, 103b of differing types are disposed in concentric circles, then it becomes easy to avoid the situation in which, for example, if being used to administer medicines, the microneedles of either medicine type no longer make contact.

Here, an explanation was given for the case in which the microneedles 103a of the two first areas Ar3, Ar5 are the same; however, it is also possible to make the types (the types and the amounts of the contained compositions) of the microneedles of the two first areas Ar3, Ar5 different, and to make the area indicated by Ar5a third area. For example, if being used in the field of medical care, a configuration is possible such that 20 wt % of a pharmaceutical agent α is administered by the microneedles of the first area Ar3, 35 wt % of a pharmaceutical agent β is administered by the second area Ar4, and 45 wt % of a pharmaceutical agent γ is administered by the third area.

(8-3) Modified Example 2C

The first embodiment and the second embodiment mentioned above explain the case in which the microneedles 103, 103a, 103b have a two-layer structure in which the bottom-part layers 105, 105a, 105b are formed continuous with the peak-part layers 104, 104a, 104b. However, the microneedles may have a structure having three or more layers. For example, as in microneedles 103c, 103d, 103e shown in FIG. 15A, it is also possible to form intermediate layers 106c, 106d, 106e between peak-part layers 104c, 104d, 104e and bottom-part layers 105c, 105d, 105e, respectively. Here, although they are denoted as the intermediate layers 106c, 106d, 106e, each intermediate layer can also be made into multiple layers.

If a three-layer structure is formed like the one having the microneedles 103c, 103d, 103e, then, for example, an intermediate-layer, raw-material-liquid filling step and another drying step, which dries the intermediate layers, are added between the drying step (the step S5) and the combining step (the step S20) shown in FIG. 6. In the intermediate-layer, raw-material-liquid filling step, the intermediate-layer, raw-material liquid can be filled in the same manner as in the peak-part-layer, raw-material-liquid filling step using the droplet-delivery apparatus 10. Furthermore, as in FIG. 15A, in the manufacture of the microneedle array having the three types of microneedles 103c, 103d, 103e, after the filling of the two types of microneedles 103c, 103d using the droplet-delivery apparatus 10 has ended, then the cartridge 13a or the cartridge 13b may be exchanged and the filling of the one additional type of microneedle 103e may be performed; however, if another droplet-delivery apparatus (not shown) is used that further comprises a third nozzle apart from the nozzles 11a, 11 b and a third cartridge apart from the cartridges 13a, 13b, then the time taken to exchange the cartridge can be omitted, and thereby the manufacturing time can be shortened.

In addition, like the peak-part-layer, raw-material liquid, the intermediate-layer, raw-material liquid is, for example: a solution into which a solid raw material is dissolved into water, a mixed solvent of water and alcohol, or some other solvent; a suspension in which a solid raw material is dispersed into water, a mixed solvent of water and alcohol, or some other solvent; or a liquid mixture thereof.

A microneedle array 110C can also be configured by disposing the microneedles 103c described above in a first area Ar6 shown in FIG. 15B, disposing the microneedles 103d in a second area Ar7, and disposing the microneedles 103e in a third area Ar8. Alternatively, a microneedle array 110D can be configured by disposing the microneedles 103c in a first area Ar9 shown in FIG. 15C, disposing the microneedles 103d in a second area Ar10, and disposing the microneedles 103e in a third area Ar11.

In such a case, focusing on the first microneedles 103c disposed in the first areas Ar6, Ar9 and the second microneedles 103d disposed in the second areas Ar7, Ar10, the type of the (the third composition) of the intermediate layers 106c of the first microneedles 103c can be made different from the type of the composition (the first composition) of the peak-part layers 104c of the first microneedles 103c, and the type of the composition (the fourth composition) of the intermediate layers 106d of the second microneedles 103d can be made different from the type of the composition (the second composition) of the peak-part layers 104d of the second microneedles 103d. Furthermore, at least one among the type and the amount of the composition (the second composition) of the peak-part layers 104d of the second microneedles 103d can be made different from that of the composition (the first composition) of the peak-part layers 104c of the first microneedles 103c. Furthermore, at least one among the type and the amount of the composition (the third composition) of the intermediate layers 106c of the first microneedles 103c and the (the fourth composition) of the intermediate layers 106d of the second microneedles 103d can be made different. Furthermore, here, the intermediate layers 106c, 106d correspond to the second layers.

Furthermore, if used in the field of medical care, then a pharmaceutical can be composed that consists of: a first pharmaceutical agent α1 in the first microneedles 103c, wherein the peak-part layers 104c contain a first component P1 and the intermediate layers 106c contain a second component P2; a second pharmaceutical agent β1 in the second microneedles 103d, wherein the peak-part layers 104d contain a third component Q1 and the intermediate layers 106d contain a fourth component Q2; and a third pharmaceutical agent γ1 in the third microneedles 103e, wherein the peak-part layers 104e contain a fifth component R1 and the intermediate layers 106e contain a sixth component R2. In this pharmaceutical, for example, the weights of the first microneedles 103c, the second microneedles 103d, and the third microneedles 103e as well as their densities in their areas are made the same, and the dosage can be adjusted by the ratio of the surface area of the first areas Ar6, Ar9 to the surface area of the second areas Ar7, Ar10 to the surface area of the third areas Ar8, Ar11. For example, if the ratio of the surface area of the first areas Ar6, Ar9 to the surface area of the second areas Ar7, Ar10 to the surface area of the third areas Ar8, Ar11 is given by 4:7:9, then a pharmaceutical can be prepared that contains 20 wt % of the pharmaceutical agent α1, 35 wt % of the pharmaceutical agent β1, and 45 wt % of the pharmaceutical agent γ1.

(8-4) Modified Example 2D

FIG. 13 shows a case wherein the first area Ar3 is included in a concentric circle in the second area Ar4, but the aspect in that the first area Ar3 is included in the second area Ar4 is not limited thereto. For example, the microneedle arrays can also be configured such that they exhibit a sea-island structure wherein multiple first areas are scattered like islands in a sea of second areas.

Third Embodiment (9) Overview of Method of Manufacturing the Microneedle-Array Manufacturing Apparatus The first embodiment and the second embodiment mentioned above explain cases in which, to perform filling for the same microneedles, one of the nozzles 11a, 11b is used; however, the nozzles may be disposed in an array in order to jointly fill a plurality of the recessed parts 81 for the same microneedles.

Figure 16:
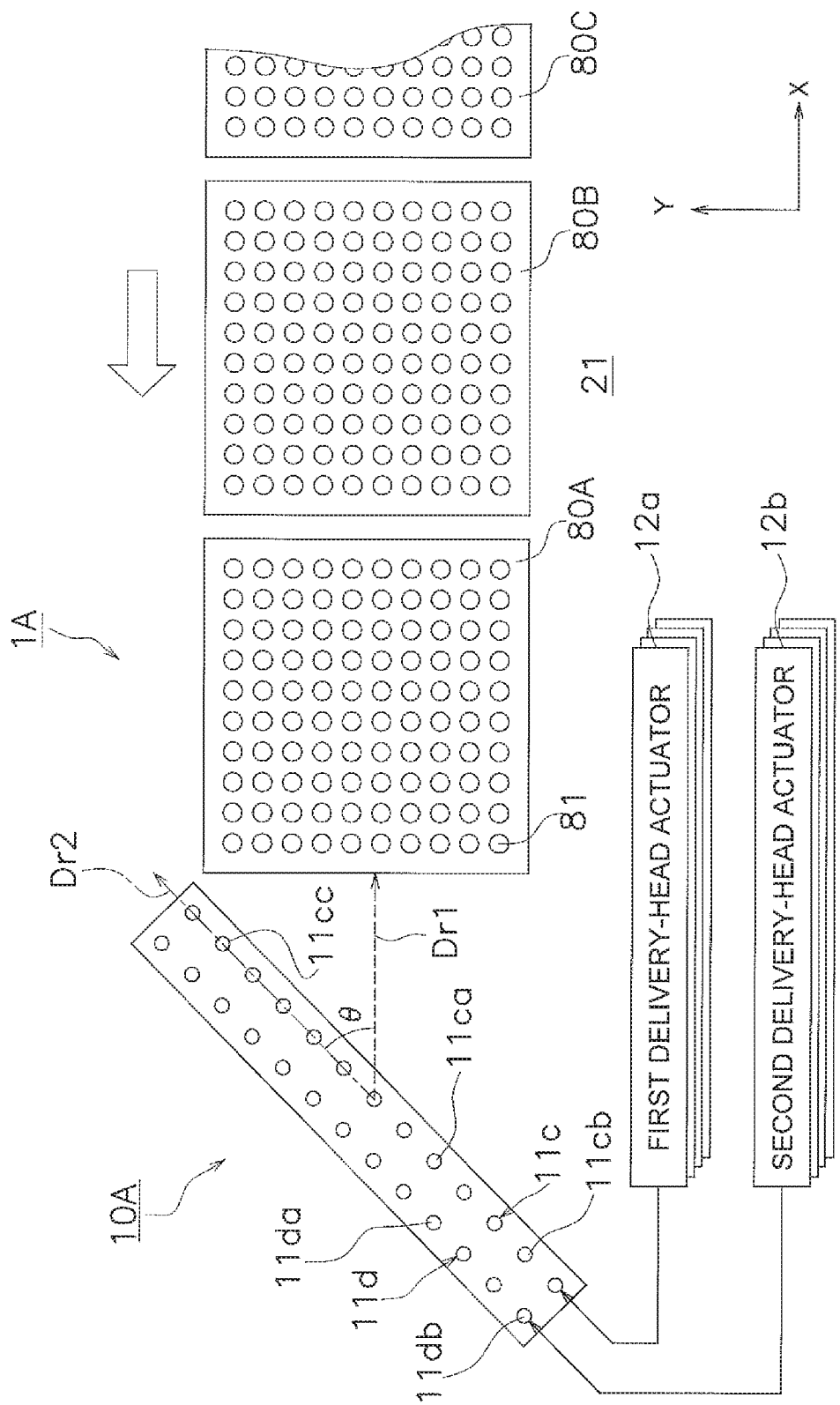
FIG. 16 is a conceptual diagram for explaining the microneedle-array manufacturing apparatus according to a third embodiment.

A droplet-delivery apparatus 10A according to the third embodiment shown in FIG. 16 comprises nozzles 11c, 11d, which are disposed in an array. Thirteen of the first delivery-head actuators 12a are attached to thirteen of the nozzles 11c, and thirteen of the second delivery-head actuators 12b are attached to thirteen of the nozzles 11d.

Moreover, molds 80A, 80B, 80C, which are mounted on one XYZ stage 21 and successively move in the X axial direction, each have ten recessed parts 81 in the X axial direction and ten recessed parts 81 in the Y axial direction arranged in a matrix.

Focusing on one column of a plurality of the recessed parts 81 lined up parallel to the X axis, for example, droplets can be delivered to the one column of recessed parts 81 by a nozzle 11ca and a nozzle 11da shown in FIG. 16. Thus, the configuration when focusing on just one column in this manner is the same as that of the droplet-delivery apparatus 10 according to the second embodiment that was explained using FIG. 10. Accordingly, if each column of the recessed parts 81 is filled as in the second embodiment, then the peak-part-layer, raw-material-liquid filling step (the step S4) shown in FIG. 6 can be implemented.

At this time, with regard to nozzles for which corresponding recessed parts 81 do not exist in the mold 80, for example, nozzles 11cb, 11db, control is performed such that the operation of the corresponding first delivery-head actuator 12a is stopped and the operation of the corresponding second delivery-head actuator 12b is stopped, and thereby droplets are not delivered.

Because the molds 80A, 80B, 80C move continuously, the state arises in which, when the nozzle 11ca of one nozzle array is delivering to the mold 80A, another nozzle 11cc is delivering to the following mold 80B. The droplet-delivery apparatus 10A thus simultaneously delivers to a plurality of the molds 80A, 80B continuously, and thereby the filling time of the droplet-delivery apparatus 10A can be shortened.

In addition, in the manufacture of another lot, if droplets are delivered to molds in which the layout spacings of the recessed parts 81 differ, then an angle θ formed by a direction Dr2, in which the nozzles 11c, 11d of the droplet-delivery apparatus 10A are lined up, and a relative-movement direction Dr1 of the nozzles 11c, 11d can be adjusted by the θ-axis stepping motor 21d shown in FIG. 2. Thereby, the Y coordinate of each nozzle of the plurality of nozzles 11c, 11d and the Y coordinate of the plurality of recessed parts 81 can be made to coincide.

Furthermore, unillustrated portions of a microneedle-array manufacturing apparatus 1A shown in FIG. 16 can be configured the same as in the microneedle-array manufacturing apparatus 1 of the first embodiment.

(10) Modified Examples (10-1) Modified Example 3A

The abovementioned third embodiment explained a case in which the nozzles 11c, 11d are disposed lined up in two columns, but a configuration is also possible such that the droplet-delivery apparatus 10A has three or more columns of the nozzles. In addition, the droplet-delivery apparatus 10A can also be modified such that the nozzles 11c alone are disposed lined up in one column.

(10-2) Modified Example 3B

In the abovementioned third embodiment, the plurality of recessed parts 81 is disposed in a square shape; however, if the plurality of recessed parts 81 is disposed in a circular shape, then a configuration is also possible such that delivery is performed while the mold is being rotated in the θ direction.

(11) Features 11-1

As explained above, the microneedle-array manufacturing apparatuses 1, 1A are apparatuses for forming the microneedle arrays 110, 110A-110E, which comprise the microneedles 103, 103a-103f, by filling the plurality of recessed parts 81, which are formed in the molds 80, 80A, 80B, 80C, with the raw-material liquid for forming the microneedles 103, 103a-103f and comprise the droplet-delivery apparatuses 10, 10A and the aligning apparatus 20. Using the XYZ stage 21 of the aligning apparatus 20, the aligning apparatus 20 aligns the relative positions of the nozzles 11a, 11b, 11c, 11d of the droplet-delivery apparatuses 10, 10A with the mold 80 such that, as shown in, for example, FIG. 8, the droplets from the droplet-delivery apparatuses 10, 10A are caused to land in each of the recessed parts 81. Furthermore, the droplet-delivery apparatuses 10, 10A perform filling by delivering the droplets 91a-91e of the peak-part-layer, raw-material liquid 91, for example, as shown in FIG. 8, a prescribed amount at a time to each recessed part 81, wherein the prescribed amount is less than the capacity of the relevant recessed part 81.

Looking at this from the viewpoint of the microneedle-array manufacturing method, the peak-part-layer, raw-material-liquid filling step (the step S4) shown in FIG. 6 is a first filling step in which the plurality of recessed parts 81 is filled with the peak-part-layer, raw-material liquid 91 by causing the droplets 91a-91e of the peak-part-layer, raw-material liquid 91 (an example of a first raw-material liquid), in an amount less than the capacity of the recessed part 81, to land in the plurality of recessed parts 81 (an example of first recessed parts) of the molds 80, 80A-80C. In addition, the drying step (the step S5) in FIG. 6 is a drying step in which the peak-part-layer, raw-material liquid 91 of the plurality of recessed parts 81 is dried, and thereby the microneedle arrays 110, 110A-110E comprising the plurality of microneedles 103, 103a-103f are formed.

Thus, by adjusting the total amount of the droplets 91a-91e delivered per single recessed part 81, the amount of the peak-part-layer, raw-material liquid 91 per single recessed part 81 is adjusted with good accuracy. Because the concentration of the composition in the peak-part-layer, raw-material liquid 91 is substantially constant, the amounts of the composition contained in the peak-part layers 104, 104a-104e created by the solidification of the peak-part-layer, raw-material liquid 91 as the raw material are adjusted with good accuracy. As a result, the distribution of the composition of the microneedle arrays 110, 110A-110E is adjusted with good accuracy.

11-2

As described above, each of the droplet-delivery apparatuses 10, 10A is configured capable of delivery such that the plurality of droplets 91*a*-91*e* is less than the capacity of each recessed part 81, as shown in FIG. 8. If the recessed part 81 is filled with the peak-part-layer, raw-material liquid 91 in one droplet, then in the case of the conical recessed part 81 like that shown in FIG. 8, bubbles tend to form in the bottom part, the peak-part-layer, raw-material liquid 91 tends to spill out of the recessed part 81 owing to the reaction when it lands, or the like. In contrast, if filling is performed with a plurality of droplets, then bubbles tend not to be formed in the bottom part and spilling out of the recessed part 81 tends not occur, and therefore it becomes easy to adjust the fill amount with good accuracy.

11-3

In the case shown in FIG. 8 described above, a case is explained in which the five droplets 91*a*-91*e* fully fill one recessed part 81, but each of the droplet-delivery apparatuses 10, 10A is adjustably configured such that the liquid amount of one droplet delivered at one time is less than one third of the capacity of each recessed part 81. Furthermore, it is configured such that each of the droplet-delivery apparatuses 10, 10A and the aligning apparatus 20 can be aligned such that three or more droplets land at differing positions inside the recessed part 81. For example, in the case shown in FIG. 8, the landing locations are the landing points Lp1-Lp5, which differ from one another. Thus, by virtue of the positions at which the droplets 91*a*-91*e* land being different, even if the viscosity of the peak-part-layer, raw-material liquid 91 is high, the generation of bubbles inside the recessed part 81 is suppressed and spill-out can be prevented.

11-4

As explained in the abovementioned second embodiment and third embodiment, by putting the peak-part-layer, raw-material liquid 91 (an example of a first liquid) and the peak-part-layer, raw-material liquid 93 (an example of a second liquid) in the cartridges 13*a*, 13*b*, each of the droplet-delivery apparatuses 10, 10A can separately deliver—using the nozzle 11*a* and the nozzle 11*b* or the nozzles 11*c* and the nozzles 11*d*—the peak-part-layer, raw-material liquids 91, 93, whose components differ from one another, as the raw-material liquids. As a result, it becomes possible to easily form the various modes of the microneedle arrays 110, 110A-110E, as shown in, for example, FIG. 4, FIG. 11 to FIG. 15A, FIG. 15B, FIG. 15C, and FIG. 17A and FIG. 17B, by combining the various microneedles 103, 103*a*-103*f*.

11-5

As was explained using FIG. 10 to FIG. 4415, each of the droplet-delivery apparatuses 10, 10A and the aligning apparatus 20 are configured such that each of the recessed parts 81 located in the first areas Ar1, AR3, Ar5, Ar6, Ar9 of the mold 80 is filled with just a first amount of the raw-material liquid and such that each of the recessed parts 81 located in the second areas Ar2, AR4, Ar7, and Ar10 of the mold 80 is filled with just a second amount of the raw-material liquid. As a result, the amounts of the composition in the first areas Ar1, AR3, Ar5, Ar6, Ar9 and the amounts of the composition in the second areas Ar2, AR4, Ar7, and Ar10 can be controlled with good accuracy.

11-6

The recessed parts 81 in which the peak-part-layer, raw-material liquids 93 land as explained using FIG. 10 can be regarded as second recessed parts. If so regarded, then the peak-part-layer, raw-material-liquid filling step (the step S4) of FIG. 6 for filling the peak-part-layer, raw-material liquid 93 is a second filling step in which a droplet of the peak-part-layer, raw-material liquid 93 (an example of the second raw-material liquid) in an amount less than the capacity of each recessed part 81 is caused to land in every recessed part 81 of the mold 80, thereby filling the recessed parts 81 with the peak-part-layer, raw-material liquid 93. In addition, the drying step (the step S5) in FIG. 6 can be regarded as a drying step in which the peak-part-layer, raw-material liquid 93 in the plurality of recessed parts 81 is dried, thereby forming the microneedle arrays 110A-110E comprising the plurality of microneedles 103*a*-103*f*.

In this case, the areas in which the microneedles manufactured from the peak-part-layer, raw-material liquid 91 (an example of the first raw-material liquid) are arranged and the areas in which the microneedles manufactured from the peak-part-layer, raw-material liquid 93 (an example of the second raw-material liquid) are arranged can be variously combined, and thereby it becomes possible to manufacture a variety of microneedle arrays.

Figure 15A:
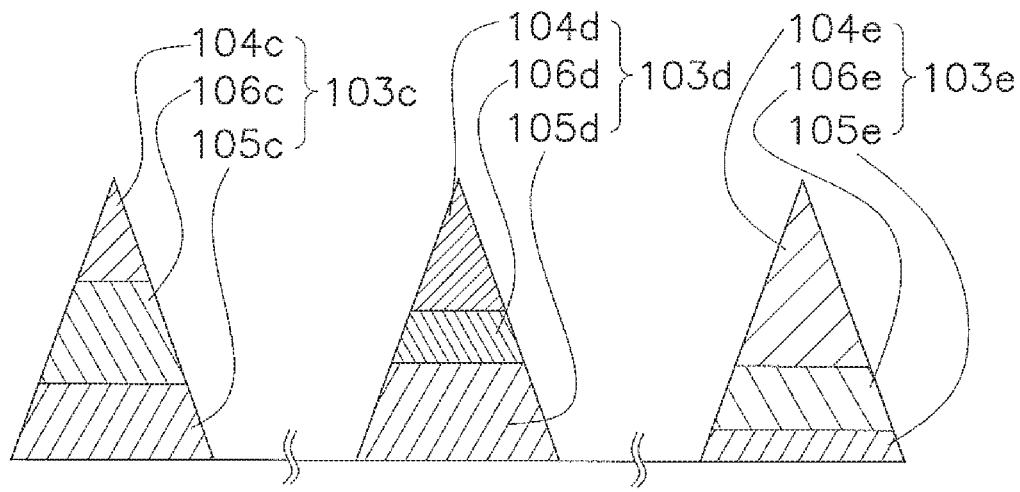
FIG. 15A is a schematic cross-sectional view for explaining, according to a modified example 2C, the microneedle array.
Figure 15B:
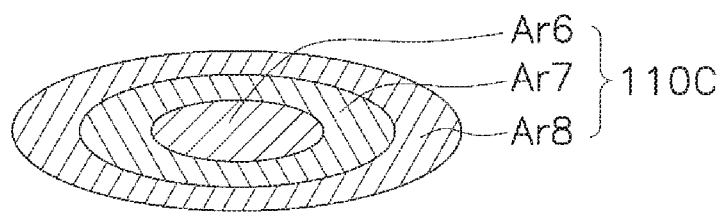
FIG. 15B is a conceptual diagram for explaining, according to the modified example 2C, one example of the product having the microneedle array.
Figure 15C:
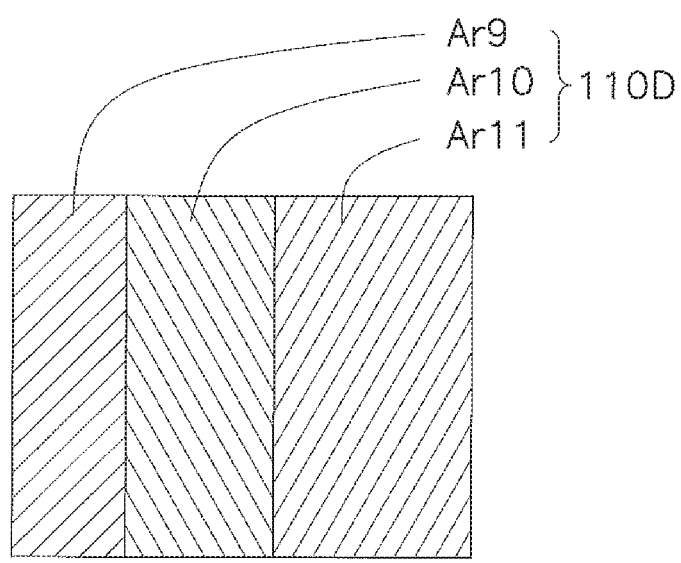
FIG. 15C is a conceptual diagram for explaining, according to the modified example 2C, another example of the product having the microneedle array.

In addition, as in the modified example 2C that was explained using FIG. 15A FIG. 15B and FIG. 15C, the recessed parts 81 partly buried by the solid body formed by the drying of the peak-part-layer, raw-material liquids 91, 93 (examples of the first raw-material liquid) can be regarded as the second recessed parts. That is, the intermediate-layer, raw-material-liquid filling step of the modified example 2C is the second filling step in which a droplet of the intermediate-layer, raw-material liquid in an amount less than the capacity of each recessed part 81 (in this case, the capacity resulting from subtracting the volume of the solid body created by the drying of the peak-part-layer, raw-material liquids 91, 93) is caused to land in every recessed part (an example of the second recessed part) of the mold 80 wherein the peak-part-layer, raw-material liquids 91, 93 have dried, thereby filling every recessed part 81 with the intermediate-layer, raw-material liquid. In addition, the drying step of the intermediate-layer, raw-material liquid can be regarded as a drying step in which the intermediate-layer, raw-material liquid of the plurality of recessed parts 81 is dried, thereby forming the microneedle arrays 110A-110E comprising the plurality of microneedles 103*a*-103*f*.

In this case, the peak-part layers 104*c*, 104*d*, 104*e* manufactured from the peak-part-layer, raw-material liquids 91, 93 (examples of the first raw-material liquid) and the intermediate layers 106*c*, 106*d*, 106*e* manufactured from the intermediate-layer, raw-material liquid (an example of the second raw-material liquid) can be variously combined, and thereby it becomes possible to manufacture a variety of the microneedle arrays 110C, 110D.

11-7

The combining step (the step S20) and the drying and sticking (the step S21) in FIG. 6 are a fastening step in which the porous-base member 85, at least part of the surface of which is covered by the bottom-part-layer, raw-material liquid 92 (an example of a third raw-material liquid), is overlaid on the surface on which the recessed parts 81 of the mold 80 are formed, the bottom-part-layer, raw-material liquid 92 is dried, and thereby the microneedles 103*a*-103*f*, which include the portions formed by the drying of the peak-part-layer, raw-material liquids 91, 93, are fastened onto the porous-base member 85.

At least part of the surface of the porous-base member 85 is covered by the bottom-part-layer, raw-material liquid 92, and therefore it becomes easy for the bottom-part-layer, raw-material liquid 92 to penetrate the interior of the holes of the porous-base member 85, and it becomes easy to form the products 100, 100A having the microneedles securely fixed to the porous-base member 85. That result is improved by providing the curing step (the step S15) prior to the fastening step.

11-8

For example, as was explained using FIG. 11 to FIG. 15A, FIG. 15B and FIG. 15C, the first microneedles 103a, 103c are formed in at least one of the first areas Ar1, Ar3, Ar5, Ar6, Ar9, and contain the first composition in the peak-part layers 104a, 104c at the tips and contain the third composition in the following bottom-part layers 105a (examples of a second layer of a first microneedle) or the following intermediate layers 106c (examples of the second layer of the first microneedle). In addition, the second microneedles 103b, 103d are formed in at least one of the second areas Ar2, Ar4, Ar7, Ar10 adjacent to the first areas Ar1, Ar3, Ar5, Ar6, Ar9 and contain the second composition in the peak-part layers 104b, 104d at the tips and contain the fourth composition in the following bottom-part layers 105b (examples of a second layer of a second microneedle) or in the following intermediate layers 106d (examples of the second layer of the second microneedle). Furthermore, by using the microneedle-array manufacturing apparatus and the microneedle-array manufacturing method described above, a configuration becomes possible such that: the type of the third composition differs from that of the first composition and the type of the fourth composition differs from that of the second composition; at least one among the type and the amount of the second composition differs from that of the first composition; and at least one among the types and the amounts of the third composition and the fourth composition differs.

As a result, if the product 100, 100A and 100B 100C, 100D having the microneedle arrays is used in the field of, for example, medical care, then it becomes possible to handle the preparation of a variety of pharmaceutical agents and to use them in various administration situations.

11-9

In addition, by using the microneedle-array manufacturing apparatus and the microneedle-array manufacturing method described above, a configuration is possible such that at least one of the second areas Ar2, AR4, Ar7 is disposed such that it surrounds at least one of the first areas Art, AR3, Ar6. As a result, in the products 100, 100A and 100B having the microneedle arrays, it is possible to prevent the problem wherein, for example, when all the microneedles have not come in contact with the skin, the microneedles of only one area are used.

11-10

As was explained as the modified example 1C using FIG. 17A and FIG. 17B described above, a product 100E having the microneedle array comprises the fixed part 109f and the plurality of microneedles 103f. The surface 102f of the fixed part 109f has a curved three-dimensional shape as in a concave mirror. Consequently, the plurality of microneedles 103f likewise is three dimensionally disposed, along a curved three-dimensional shape as in a concave mirror, on the surface 102f of the fixed part 109f. Moreover, because the microneedles 103f are disposed parallel to one another, all the microneedles 103f in the pushing direction tend to extend and stick. In addition, it becomes easy to attach also to comparatively small locations having complex three-dimensional shapes as in, for example, an ear.

Fourth Embodiment

Figure 19:
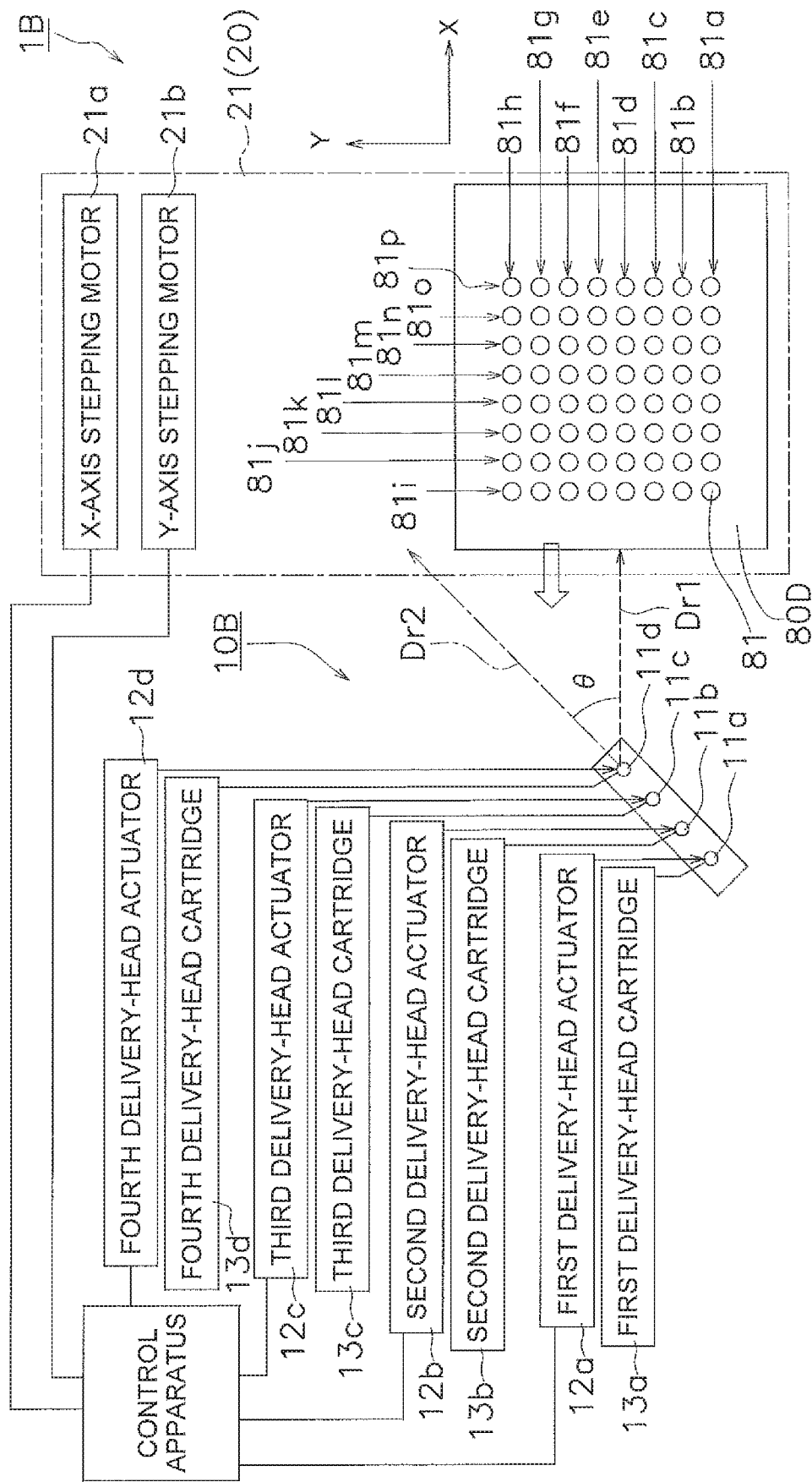
FIG. 19 is a conceptual diagram for explaining the microneedle-array manufacturing apparatus according to a fourth embodiment.

(12) Overview of Method of Manufacturing the Microneedle-Array Manufacturing Apparatus The droplet-delivery apparatus 10A according to the abovementioned third embodiment comprises, as shown in FIG. 16, the nozzles 11c, 11d, which are disposed in an array, and has thirteen first delivery-head actuators 12a and thirteen second delivery-head actuators 12b corresponding to the thirteen nozzles 11c, 11d, respectively. However, the structure can be made slightly simpler than that of the droplet-delivery apparatus 10A according to the third embodiment. A droplet-delivery apparatus 10B of a microneedle-array manufacturing apparatus 1B according to a fourth embodiment shown in FIG. 19 has a structure simpler than that of the droplet-delivery apparatus 10A of the microneedle-array manufacturing apparatus 1A according to the third embodiment. In addition, the microneedle-array manufacturing apparatus 1B also comprises other structural elements, such as the microneedle-array manufacturing apparatus 1 according to the first embodiment and the second embodiment, the CCD camera 22 and the alignment monitor 23 of the microneedle-array manufacturing apparatus 1A according to the third embodiment, and the like; however, descriptions thereof are omitted in FIG. 19.

The droplet-delivery apparatus 10B comprises the four nozzles 11a, 11b, 11c, 11d. Droplets are delivered from these four nozzles 11a, 11b, 11c, 11d by the first delivery-head actuator 12a, the second delivery-head actuator 12b, a third delivery-head actuator 12c, and a fourth delivery-head actuator 12d, respectively.

In addition, raw-material liquid is delivered from the cartridge 13a for a first delivery head, the cartridge 13b for a second delivery head, a cartridge 13c for a third delivery head, and a cartridge 13d for a fourth delivery head to the four nozzles 11a, 11b, 11c, 11d, respectively, of the droplet-delivery apparatus 10B. Raw-material liquids of differing types can be placed in the four cartridges 13a, 13b, 13c, 13d, or the same type of raw-material liquid can be placed therein.

In a mold 80D, the recessed parts 81 are arranged in a matrix, eight in the X axial direction and eight in the Y axial direction. Each recessed part 81 of the mold 80D belongs to one of the first to eighth rows, that is, recessed parts 81a, 81b, 81c, 81d, 81e, 81f, 81g, 81h, and simultaneously belongs to one of the first to eighth columns, that is, recessed parts 81i, 81j, 81k, 81l, 81m, 81n, 81o, 81p. The mold 80D is mounted on the XYZ stage 21, and the movement of the XYZ stage 21 explained below is only movement in the X axial direction and movement in the Y axial direction, and therefore any description of the Z-axis stepping motor 21c is omitted in FIG. 19.

In the microneedle-array manufacturing apparatus 1B, to deliver the raw-material liquid to the 64 recessed parts 81 of the mold 80D, the operation of the XYZ stage 21 in the X axial direction and the Y axial direction is stored in memory (not shown) of the control apparatus 30. For example, data that indicates the positions of the 64 recessed parts 81, using the alignment marks 83 as a reference, are stored in the control apparatus 30. Here, because the shape of every recessed part 81 is the same, data about the shape of one recessed part 81, in particular, the diameter of the circular recessed part 81 in a plan view, is stored.

Based on these data, the control apparatus 30 performs controls such that, for example, 32 of the recessed parts, from the first row of recessed parts 81a to the fourth row of recessed parts 81d, are filled with the raw-material liquid by the four nozzles 11a-11d while the stage 21 is moved at a constant velocity in the X axial direction. Next, the stage 21 is moved in the Y axial direction to align the Y axial direction positions of the fifth-row recessed part 81e to the eighth-row recessed part 81h with the positions of the four nozzles 11a-11d in the Y axial direction. Furthermore, the control apparatus 30 once again performs control such that the 32 recessed parts from the fifth-row recessed part 81e to the eighth-row recessed part 81h are filled with the raw-material liquid by the four nozzles 11a-11d while the stage 21 is moved at a constant velocity in the X axial direction.

If, apart from the peak-part layers, one or a plurality of the intermediate layers, in which the type of the raw-material liquid is different, is formed, then the filling step described above is performed as the peak-part-layer, raw-material-liquid filling step (the step S4) shown in FIG. 6, after which, for example, the cartridges 13a, 13b, 13c, 13d are replaced and the raw-material liquid in the nozzles is switched from the peak-part-layer, raw-material liquid to the intermediate-layer, raw-material liquid. Subsequently, the drying step (the step S5) is performed, and the microneedle-array manufacturing apparatus 1B fills 64 of the recessed parts 81, in accordance with the procedure described above, with the intermediate-layer, raw-material liquid using the cartridges 13a, 13b, 13c, 13d containing the intermediate-layer, raw-material liquid. In so doing, the previously explained intermediate-layer, raw-material-liquid filling step and the other drying step, in which the intermediate layers are dried, are added.

Furthermore, the microneedle-array manufacturing method according to the fourth embodiment can also be performed in accordance with the step S1 to the step S21 shown in FIG. 6, the same as in the microneedle-array manufacturing method according to the first embodiment.

Next, the delivery of droplets to one row of the recessed parts 81 will be explained, using FIG. 20 and FIG. 21. The nozzle 11a shown in FIG. 20 delivers droplets while moving, as the stage 21 moves, in the X axial direction at a constant velocity relative to the mold 80D. Based on the data stored in the memory and based on the alignment marks 83, the control apparatus 30 controls the delivery of the droplets while judging whether the nozzle 11a is, for example, positioned above the first-row recessed parts 81a or positioned between two of the recessed parts 81a adjacent to one another.

Figure 20:
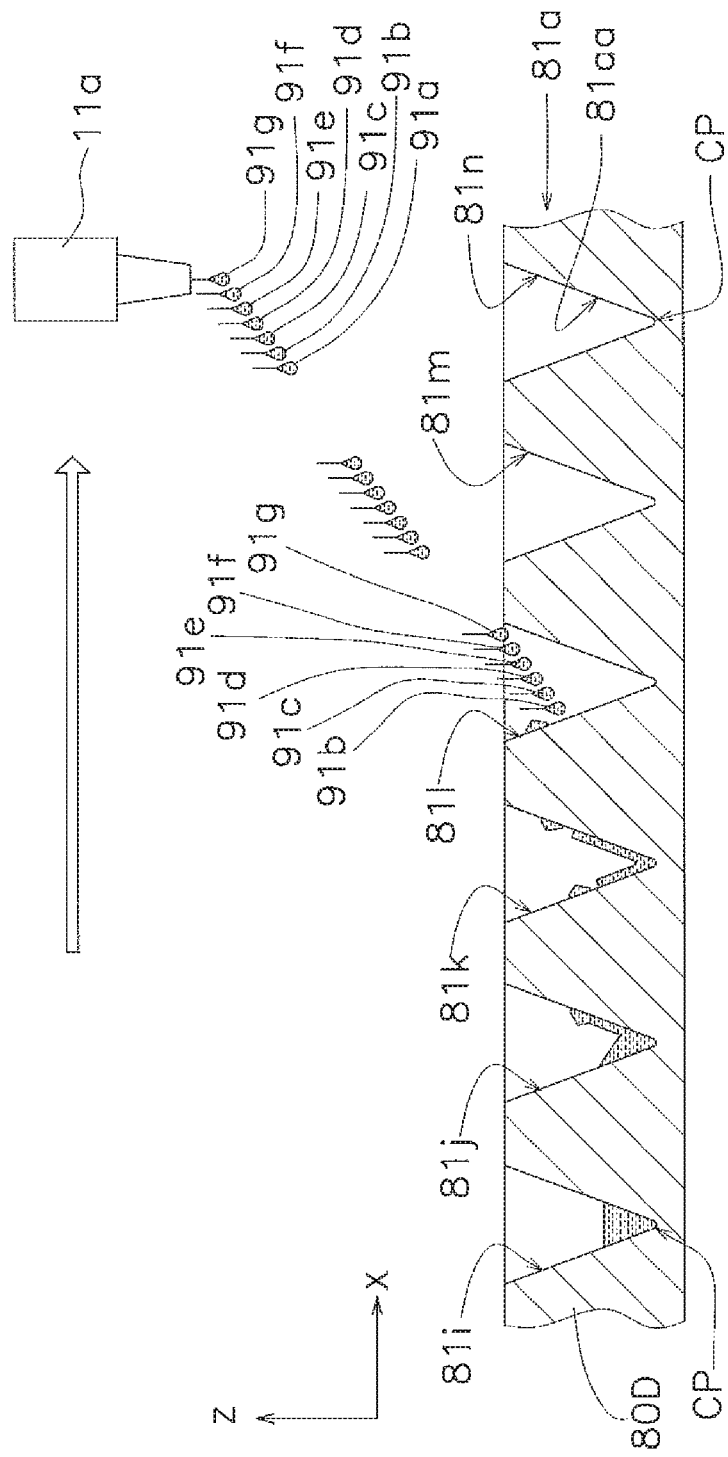
FIG. 20 is a schematic cross-sectional view for explaining the delivery of droplets to the recessed parts.
Figure 21:
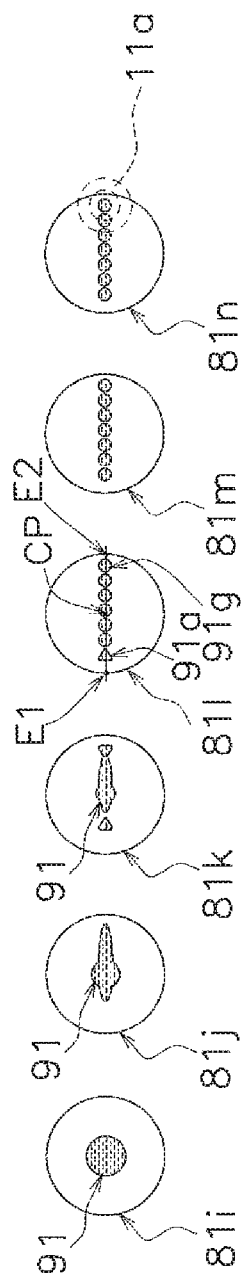
FIG. 21 is a schematic plan view for explaining the delivery of droplets to the recessed parts.

FIG. 20 and FIG. 21 show the state in which droplets have already landed in the first-column recessed part 81i, the second-column recessed part 81j, and the third-column recessed part 81k, and thus are already filled with the peak-part-layer, raw-material liquid 91. In addition, the state is shown in which, in the fourth-column recessed part 81l, one droplet has landed and the remaining six droplets 91b, 91c, 91d, 91e, 91f, 91g have not yet landed. Furthermore, the state is shown wherein, in the fifth-column recessed part 81m and the sixth-column recessed part 81n, the seven droplets 91a, 91b, 91c, 91d, 91e, 91f, 91g have not yet landed. The nozzle 11a is located above the sixth-column recessed part 81n. For example, the mold 80D is formed of a hydrophobic material, and the peak-part-layer, raw-material liquid 91 is an aqueous solution; as shown in FIG. 20 and FIG. 21, the peak-part-layer, raw-material liquid 91 tends to travel along a wall surface 81aa of each recessed part 81a and collect at a center part CP, and, as in the recessed part 81i, collects centered around the center part CP. If configured in this manner, the mold 80D is formed of, for example, a hydrophobic silicone rubber.

The control apparatus 30 verifies the position of the nozzle 11a via the alignment marks 83, and when the nozzle 11a is located above the first-column recessed part 81i, seven droplets are delivered from the nozzle 11a and land in the recessed part 81i. The nozzle 11a moves at a constant velocity as is, and when the nozzle 11a is located between the first-column recessed part 81i and the second-column recessed part 81j, the delivery of droplets from the nozzle 11a is stopped. The nozzle 11a moves at a constant velocity as is, and when the nozzle 11a is located above the second-column recessed part 81j, seven droplets are delivered from the nozzle 11a and land in the recessed part 81j. By repetitively performing such operations, all eight recessed parts 81a of the first row are filled with the peak-part-layer, raw-material liquid 91.

Viewing the operations described above from the droplets side, if the droplet 91a that lands beforehand in each recessed part 81a is regarded as a first droplet and the droplet 91b that lands next is regarded as a second droplet, then the aligning apparatus 20 aligns the relative position of the droplet-delivery apparatus 10B and the mold 80D such that the second droplet 91b lands in each recessed part 81a on the center part CP side of the first droplet 91a. In addition, it is also possible to regard the droplet 91b as the first droplet and the droplet 91c as the second droplet.

In addition, switching the viewpoint of the operations described above from the droplets side, if the droplet 91g that lands beforehand in each recessed part 81a is regarded as the $n^{th}$ droplet (where n is a natural number) and the droplet 91f that lands next is regarded as the $n-1^{th}$ droplet, then the aligning apparatus 20 aligns the relative position of the droplet-delivery apparatus 10B and the mold 80D such that the $n-1^{th}$ droplet 91f lands in each recessed part 81a on the center part CP side of the $n^{th}$ droplet 91g.

For example, to explain this using the recessed part 81l in FIG. 21, the aligning apparatus 20 aligns the relative position of the droplet-delivery apparatus 10B and the mold 80D such that the droplets 91a-91g land in the recessed part 81l at sequentially differing positions from one end E1 side of the recessed part 81l to the other end E2 side, passing through the center part CP.

The amount of the peak-part-layer, raw-material liquid 91 in each recessed part 81 can be adjusted by the number of droplets delivered to each recessed part 81. For example, when the number of droplets to be delivered per recessed part 81 becomes large, the velocity at which the stage 21 moves in the X axial direction is slowed down, and thereby the droplet amount can be increased without changing the droplet delivery interval—even though the recessed part 81 diameter is the same.

In addition, the microneedle-array manufacturing apparatus 1B is configured such that, if droplets are delivered to a mold, wherein the layout spacing of the recessed parts 81 varies, in the manufacture of another lot, then the angle θ formed by the direction Dr2, in which the nozzles 11a, 11b, 11c, 11d of the droplet-delivery apparatus 10B are lined up, and the relative-movement direction Dr1 of the nozzles 11a-11d can be adjusted by the θ-axis stepping motor 21d shown in FIG. 2. Thereby, the Y coordinates of each of the nozzles 11a-11d and the Y coordinates of the recessed parts 81 can be made to coincide.

(13) Modified Examples

(13-1) Modified Example 4A

The abovementioned fourth embodiment explained a case in which the four nozzles 11a-11d are disposed lined up in one column, but a configuration is also possible such that there are three nozzles or five or more nozzles. In addition, instead of the layout of the nozzles being in one straight line, the nozzles can also be disposed, for example, lined up along some other shape such as in a zigzag, an arcuate shape, or the like.

(13-2) Modified Example 4B

In the abovementioned fourth embodiment, the plurality of recessed parts 81 is disposed in a square shape, but a configuration is also possible such that, if the plurality of recessed parts 81 is disposed in a circular shape, then delivery can be performed while rotating the mold in the $\theta$ direction.

(13-3) Modified Example 4C

The abovementioned fourth embodiment explained a case in which the nozzle 11a moves along a line that connects the center parts CP of the one row of recessed parts 81a, but the locus through which the nozzle 11a moves is not limited to a line shape that connects the center parts CP. For example, the nozzle 11a may move such that it describes a locus that is shifted by $\Delta Y$ in the Y axial direction from the line that connects the center parts CP of the recessed parts 81a and is parallel to the line that connects the center parts CP. This applies likewise to the other nozzles 11b-11d in addition to the nozzle 11a. Furthermore, $\Delta Y$ is set to a value that is smaller than the radius of each recessed part 81a.

(14) Features

The microneedle-array manufacturing apparatus 1B according to the abovementioned fourth embodiment can likewise adjust the amount of the peak-part-layer, raw-material liquid 91 per recessed part 81 with good accuracy by adjusting the total amount of the droplets 91a-91g delivered per recessed part 81. Because the concentration of the composition in the peak-part-layer, raw-material liquid 91 is substantially constant, the amount of the composition contained in the peak-part layers created by the solidification of the peak-part-layer, raw-material liquid 91 as the raw material is adjusted with good accuracy. As a result, the distribution of the composition in the microneedle array is adjusted with good accuracy.

Furthermore, in the microneedle-array manufacturing apparatus 1B, if the droplet 91a that lands beforehand in each recessed part 81a is regarded as the first droplet and the droplet 91b that lands next is regarded as the second droplet, then it is conceivable for the aligning apparatus 20 to align the relative position of the droplet-delivery apparatus 10B and the mold 80D such that the second droplet 91b lands in each recessed part 81a on the center part CbCP side of the first droplet 91a. Thus, by virtue of the droplet-delivery apparatus 10B causing the second droplet 91b to land on the center part CP side of the first droplet 91a, the first droplet 91a adheres to the wall surface 81aa of the recessed part 81a, and therefore rather than adhering from the start, bubbles tend not to engulf the center part CP. Furthermore, because the first droplet 91a and the second droplet 91b both flow in from and along the wall surface 81aa toward the center part CP, the filling of the peak-part-layer, raw-material liquid 91 proceeds in turn from the bottom of the center part CP, and thereby it is possible to prevent bubbles from collecting at the bottom of the center part CP of the recessed part 81a.

Such functions and effects can be considered also in the case in which the droplet 91g that lands in each recessed part 81a beforehand is regarded as the $n^{th}$ droplet, the droplet 91f that lands next is regarded as the n-1$^{th}$ droplet, and the n-1th droplet 91f lands in each recessed part 81a on the center part CP side of the $n^{th}$ droplet 91g.

In addition, as was explained using FIG. 21, if the relative position of the droplet-delivery apparatus 10B and the mold 80D is aligned such that the droplets 91a-91g land in the recessed part 81l at sequentially differing positions from the one end E1 side of the recessed part 81l to the other end E2 side, passing through the center part CP, then it is possible to prevent problems such as: the droplets largely adhering excessively to the one end E1 side; the droplets largely adhering excessively to the other end E2 side; bubbles collecting at the bottom of the recessed part 81l; the peak-part-layer, raw-material liquid 91 spilling out of the recessed part 81l; and the like.

The invention claimed is:

1. A microneedle-array manufacturing method comprising:
    reading alignment marks on a surface of a mold;
    identifying positions of a plurality of first recessed parts of the mold by using the alignment marks;
    adjusting an angle formed by a first direction in which the plurality of first recessed parts of the mold are disposed in an array and a second direction in which a plurality of nozzles are disposed in an array and which is inclined relative to the first direction, by rotating, based on the positions of the plurality of first recessed parts, the mold around a center axis of a stage on which the mold is disposed, the center axis extending in a vertical direction that is perpendicular to the first and second directions;
    a first filling step in which the plurality of first recessed parts are filled with a first raw-material liquid by causing at least one of the plurality of nozzles to deliver, in the plurality of first recessed parts, a plurality of droplets of the first raw-material liquid in an amount that is less than the capacity of the first recessed part to cause the plurality of droplets of the first raw-material liquid to land in the plurality of first recessed parts such that a second droplet lands in each of the first recessed parts on a center part side of a first droplet; and
    a drying step in which the first raw-material liquid of the plurality of the first recessed parts is dried, thereby forming a microneedle array comprising a plurality of microneedles.

2. The microneedle-array manufacturing method according to claim 1, further comprising
    a second filling step in which second recessed parts of the mold are filled with a second raw-material liquid by causing at least the one of the plurality of nozzles to deliver, in the second recessed parts, a plurality of droplets of the second raw-material liquid in amounts less than the capacity of each second recessed part to cause the plurality of droplets of the second raw-material liquid to land in the second recessed parts;
wherein,
the drying step includes a step of forming the microneedles by drying the second raw-material liquid in the second recessed parts.

3. The microneedle-array manufacturing method according to claim 1, further comprising
a fastening step in which a third raw-material liquid is disposed on a surface of a porous-base member such that the third raw-material liquid covers at least part thereof, the mold is reversed, a surface on which the first recessed parts of the mold are formed is overlaid on the surface of the porous-base member with a prescribed pressure, and the third raw-material liquid is dried, and thereby microneedles, which include portions formed by the drying of the first raw-material liquid, are fastened onto the porous-base member.

4. A microneedle-array manufacturing method comprising:
arranging a plurality of molds including at least a first mold and a second mold that is independent of and separate from the first mold on a stage such that the first mold and the second mold are adjacent to each other, each of the first mold and the second mold having a plurality of first recessed parts,
reading alignment marks on surfaces of the first and second molds;
identifying positions of the plurality of first recessed parts of the first and second molds by using the alignment marks;
adjusting an angle formed by a first direction in which at least one of the plurality of first recessed parts of the first mold and at least one of the plurality of first recessed parts of the second mold are arranged and a second direction in which a plurality of nozzles are disposed in an array and which is inclined relative to the first direction, by rotating, based on the positions of the plurality of first recessed parts, the first and second molds around a center axis of the stage, the center axis extending in a vertical direction that is perpendicular to the first and second directions;
a first filling step in which the at least one of the plurality of first recessed parts of the first mold and the at least one of the plurality of first recessed parts of the second mold are simultaneously filled with a first raw-material liquid by causing a plurality of droplets of the first raw-material liquid in an amount that is less than the capacity of the first recessed part to land in at least the one of the plurality of first recessed parts of the first mold and at least the one of the plurality of first recessed parts of the second mold such that a second droplet lands on a center part side of a first droplet in each of at least the one of the plurality of first recessed parts of the first mold and at least the one of the plurality of first recessed parts of the second mold; and
a drying step in which the first raw-material liquid of at least the one of the plurality of first recessed parts of the first mold and at least the one of the plurality of first recessed parts of the second mold is dried, thereby forming a microneedle array comprising a plurality of microneedles.

5. The microneedle-array manufacturing method according to claim 1, wherein
the first raw-material liquid has the viscosity that is set to a range of from 1 mPa·sec to 10 mPa·sec.

6. The microneedle-array manufacturing method according to claim 1, wherein
each of the plurality of droplets has a different landing point that does not overlap to decrease the drying time of each droplet.

7. A microneedle-array manufacturing method comprising:
reading alignment marks on a surface of a mold;
identifying, by using the alignment marks, positions of a plurality of first recessed parts of the mold, which are disposed in a matrix along a first direction and an intersecting direction intersecting the first direction;
adjusting an angle formed by the first direction and a second direction along which a plurality of nozzles that are disposed in an array and which is inclined relative to the first and intersecting directions, by rotating, based on the positions of the plurality of first recessed parts, the mold around a center axis of a stage on which the mold is disposed, the center axis extending in a vertical direction that is perpendicular to the first, second, and intersecting directions;
a first filling step in which the plurality of first recessed parts of the mold are filled with a first raw-material liquid by causing simultaneously at least two nozzles of the plurality of nozzles that face at least two recessed parts of the plurality of first recessed parts, respectively, to deliver, in at least the two recessed parts, a plurality of droplets of the first raw-material liquid in an amount that is less than the capacity of the first recessed part and causing the plurality of droplets of the first raw-material liquid to land in at least the two recessed parts such that a second droplet lands in each of at least the two recessed parts on a center part side of a first droplet; and
a drying step in which the first raw-material liquid of the plurality of the first recessed parts is dried, thereby forming a microneedle array comprising a plurality of microneedles.

8. The microneedle-array manufacturing method according to claim 4, further comprising
a second filling step in which second recessed parts of the mold are filled with a second raw-material liquid by causing the droplets of the second raw-material liquid in amounts less than the capacity of each second recessed part to land in the second recessed parts;
wherein,
the drying step includes a step of forming the microneedles by drying the second raw-material liquid in the second recessed parts.

9. The microneedle-array manufacturing method according to claim 1, wherein
the first raw-material liquid has a viscosity that is set to a range of from 0.1 mPa·sec to 100 mPa·sec.

* * * * *